US008221770B2

(12) United States Patent
Biemans et al.

(10) Patent No.: US 8,221,770 B2
(45) Date of Patent: Jul. 17, 2012

(54) VACCINE COMPOSITIONS COMPRISING L2 AND/OR L3 IMMUNOTYPE LIPOOLIGOSACCHARIDES FROM LGTB-NEISSERIA MENINGITIDIS

(75) Inventors: Ralph Biemans, Rixensart (BE); Philippe Denoel, Rixensart (BE); Christiane Feron, Rixensart (BE); Carine Goraj, Rixensart (BE); Jan Poolman, Rixensart (BE); Vincent Weynants, Rixensart (BE)

(73) Assignee: GlaxoSmithKline Biologicals s.a., Rixensart (BE)

( * ) Notice: Subject to any disclaimer, the term of this patent is extended or adjusted under 35 U.S.C. 154(b) by 0 days.

(21) Appl. No.: 12/909,621

(22) Filed: Oct. 21, 2010

(65) Prior Publication Data
US 2011/0033500 A1  Feb. 10, 2011

Related U.S. Application Data

(63) Continuation of application No. 10/523,044, filed as application No. PCT/EP03/08568 on Jul. 31, 2003, now Pat. No. 7,838,014.

(30) Foreign Application Priority Data

| Aug. 2, 2002 | (GB) | ................................. 0218035.4 |
| Aug. 2, 2002 | (GB) | ................................. 0218036.2 |
| Aug. 2, 2002 | (GB) | ................................. 0218037.0 |
| Aug. 2, 2002 | (GB) | ................................. 0218051.1 |
| Aug. 30, 2002 | (GB) | ................................. 0220197.8 |
| Aug. 30, 2002 | (GB) | ................................. 0220199.4 |
| Nov. 1, 2002 | (GB) | ................................. 0225524.8 |
| Nov. 1, 2002 | (GB) | ................................. 0225531.3 |
| Dec. 24, 2002 | (GB) | ................................. 0230164.6 |
| Dec. 24, 2002 | (GB) | ................................. 0230168.7 |
| Dec. 24, 2002 | (GB) | ................................. 0230170.3 |
| Mar. 5, 2003 | (GB) | ................................. 0305028.3 |

(51) Int. Cl.
*A61K 39/05* (2006.01)

(52) U.S. Cl. .............. 424/249.1; 424/250.1; 424/184.1; 424/193.1; 424/194.1; 424/197.11; 424/203.1; 435/172.1

(58) Field of Classification Search .......................... None
See application file for complete search history.

(56) References Cited

U.S. PATENT DOCUMENTS 6,531,131 B1  3/2003  Gu et al.

FOREIGN PATENT DOCUMENTS

| EP | 0941738 A1 | 9/1999 |
| WO | 9408021 A1 | 4/1994 |
| WO | 9610086 A1 | 4/1996 |
| WO | 0109350 A2 | 2/2001 |
| WO | 0209643 A2 | 2/2002 |

OTHER PUBLICATIONS

Li-Hui et al.; "Study on the LOS Antigenicity of 2 Candidate Strains for Meningococcal Vaccine of Serogroup B"; BIOSIS (Abstract) XP002133714; 1996.

Verheul et al.; "Preparation, Characterization, and Immunogenicity of Meningococcal Immunotype L2 and L3,7,9 Phosphoethanolamine Group-Containing Oligosaccharide-Protein Conjugates"; Infection and Immunity; 1991; vol. 59, No. 3; pp. 843-851.

Quakyi et al; "Modulation of the Biological Activities of Meningococcal Endotoxins by Association with Outer Membrane Proteins is not Inevitably Linked to Toxicity"; Infection and Immunity; 1997; vol. 65, No. 5; pp. 1972-1979.

Van Der Voort et al.; "Specificity of Human Bactericidal Antibodies against PorA P1.7,16 Induced with a Hexavalent Meningococcal Outer Membrance Vesicle Vaccine"; Infection and Immunity; 1996; vol. 64, No. 7; pp. 2745-2751.

Zakirov et al.; "Immunological Activity of Neisseria Meningitidis Lipooligosaccharide Incorporated into Liposomes"; Zhurnal Mikrobiologii Epidemiologii i Immunobiologii; 1995; vol. 0, No. 1; pp. 49-53.

Gu et al; "Preparation, Characterization and Immunogenicity of Meningococcal Lipooligosaccharide-Derived Oligosaccharide-Protein Conjugates"; Infection and Immunity; 1993; vol. 61, No. 5; pp. 1873-1880.

Jennings et al.; "Molecular Analysis of a Locus for the Biosynthesis and Phase-Variable Expression of the Lacto-N-Neotetraose Terminal Lipopolysaccharide Structure in Neisseria Meningitidis"; Molecular Microbiology; 1995; vol. 18, No. 4; pp. 729-740.

Wakarchuk et al.; "Functional Relationships of the Genetic Locus Encoding the Glycosyltransferase Enzymes Involved in Expression of the Lacto-N-Neotetraose Terminal Lipopolysaccharide Structure in Neisseria Meningitidis"; Journal of Biological Chemistry; 1996; vol. 271, No. 32; pp. 19166-19173.

*Primary Examiner* — Jennifer Graser
(74) *Attorney, Agent, or Firm* — Kathryn L. Coulter (57) ABSTRACT

The present invention relates to the field of neisserial vaccine compositions, their manufacture, and the use of such compositions in medicine. More particularly it relates to processes of making novel engineered meningococcal strains which are more suitable for the production of neisserial, in particular meningococcal, outer-membrane vesicle (or bleb) vaccines. Advantageous processes and vaccine products are also described based on the use of novel LOS subunit or meningococcal outer-membrane vesicle (or bleb) vaccines which have been rendered safer and/or more effective for use in human subjects. In particular combinations of gene downregulations are described such as PorA and OpA, PorA and OpC, OpA and OpC, and PorA and OpA and OpC. Alternatively, or in addition, lgtB⁻ is shown to be an optimal mutation for effectively and safely using L3 and/or L2 LOS in *Neisseria* vaccine compositions. Bleb vaccines derived from lgtB⁻ and capsular polysaccharide deficient meningococcal mutants are further described; as are advantageous methods of making bleb preparations where LOS is to be retained as an important antigen.

19 Claims, 5 Drawing Sheets

FIGURE 1. L3 and L2 immunotypes (H44/76, MC58 strains)

FIGURE 2. L3 and L1 immunotypes (e.g. 126E strain)

VACCINE COMPOSITIONS COMPRISING L2 AND/OR L3 IMMUNOTYPE LIPOOLIGOSACCHARIDES FROM LGTB-NEISSERIA MENINGITIDIS

CROSS-REFERENCE TO RELATED APPLICATIONS

This application is a continuation of U.S. application Ser. No. 10/523,044 filed Jul. 14, 2005, issued U.S. Pat. No. 7,838,014; which was filed pursuant to 35 U.S.C. §371 as a U.S. National Phase Application of International Patent Application No. PCT/EP03/008568 filed Jul. 31, 2003; which claims priority from Great Britain Application Nos. 0218035.4; 0218036.2; 0218037.0; 0218051.1 filed on Aug. 2, 2002; Great Britain Application Nos. 0220197.8 and 0220199.4 filed on Aug. 30, 2002; Great Britain Application Nos. 0225524.8 and 0225531.3 filed on Nov. 1, 2002; Great Britain Application Nos. 0230164.6; 0230168.7; and 0230170.3 filed on Dec. 24, 2002; and Great Britain Application No. 0305028.3 filed on Mar. 5, 2003.

FIELD OF THE INVENTION

The present invention relates to the field of neisserial vaccine compositions, their manufacture, and the use of such compositions in medicine. More particularly it relates to processes of making novel engineered meningococcal strains which are more suitable for the production of neisserial, in particular meningococcal, outer-membrane vesicle (or bleb) vaccines. Advantageous processes and vaccine products are also described based on the use of novel LOS subunit or meningococcal outer-membrane vesicle (or bleb) vaccines which have been rendered safer and more effective for use in human subjects.

BACKGROUND OF THE INVENTION

*Neisseria meningitidis* (meningococcus) is a Gram negative bacterium frequently isolated from the human upper respiratory tract. It is a cause of serious invasive bacterial diseases such as bacteremia and meningitis. The incidence of meningococcal disease shows geographical, seasonal and annual differences (Schwartz, B., Moore, P. S., Broome, C. V.; Clin. Microbiol. Rev. 2 (Supplement), S18-S24, 1989). The bacterium is commonly classified according to the serogroup if its capsular polysaccharide.

Most disease in temperate countries is due to strains of serogroup B and varies in incidence from 1-10/100,000/year total population—sometimes reaching higher values (Kaczmarski, E. B. (1997), Commun. Dis. Rep. Rev. 7: R55-9, 1995; Scholten, R. J. P. M., Bijlmer, H. A., Poolman, J. T. et al. Clin. Infect. Dis. 16: 237-246, 1993; Cruz, C., Pavez, G., Aguilar, E., et al. Epidemiol. Infect. 105: 119-126, 1990).

Epidemics dominated by serogroup A meningococci, mostly in central Africa, sometimes reach incidence levels of up to 1000/100,000/year (Schwartz, B., Moore, P. S., Broome, C. V. Clin. Microbiol. Rev. 2 (Supplement), S18-S24, 1989). Nearly all cases as a whole of meningococcal disease are caused by serogroup A, B, C, W-135 and Y meningococci, and a tetravalent A, C, W-135, Y capsular polysaccharide vaccine is available (Armand, J., Arminjon, F., Mynard, M. C., Lafaix, C., J. Biol. Stand. 10: 335-339, 1982).

The frequency of *Neisseria meningitidis* infections has risen in the past few decades in many European countries. This has been attributed to increased transmission due to an increase in social activities (for instance swimming pools, theatres, etc.). It is no longer uncommon to isolate *Neisseria meningitidis* strains that are less sensitive or resistant to some of the standard antibiotics. This phenomenon has created an unmet medical need and demand for new anti-microbial agents, vaccines, drug screening methods, and diagnostic tests for this organism.

The available polysaccharide vaccines are currently being improved by way of chemically conjugating them to carrier proteins (Lieberman, J. M., Chiu, S. S., Wong, V. K., et al. JAMA 275: 1499-1503, 1996).

A serogroup B vaccine, however, is not available. The serogroup B capsular polysaccharide has been found to be nonimmunogenic—most likely because it shares structural similarity with host components (Wyle, F. A., Artenstein, M. S., Brandt, M. L. et al. J. Infect. Dis. 126: 514-522, 1972; Finne, J. M., Leinonen, M., Mäkelä, P. M. Lancet ii.: 355-357, 1983). Effort has therefore been focused in trying to develop serogroup B vaccines from outer membrane vesicles (or blebs) or purified protein components therefrom.

Alternative meningococcal antigens for vaccine development are meningococcal lipooligosaccharides (LOS). These are outer membrane bound glycolipids which differ from the lipopolysaccharides (LPS) of the Enterobacteriaceae by lacking the O side chains, and thus resemble the rough form of LPS (Griffiss et al. Rev Infect Dis 1988; 10: S287-295). Heterogeneity within the oligosaccharide moiety of the LOS generates structural and antigenic diversity among different meningococcal strains (Griffiss et al. Inf. Immun 1987; 55: 1792-1800). This has been used to subdivide the strains into 12 immunotypes (Scholtan et al. J Med Microbiol 1994, 41:236-243) Immunotypes L3, L7, & L9 are immunologically identical and are structurally similar (or even the same) and have therefore been designated L3,7,9 (or, for the purposes of this specification, generically as "L3"). Meningococcal LOS L3,7,9 (L3), L2 and L5 can be modified by sialylation, or by the addition of cytidine 5'-monophosphate-N-acetylneuraminic acid. Although L2, L4 and L6 LOS are distinguishable immunologically, they are structurally similar and where L2 is mentioned herein, either L4 or L6 may be optionally substituted within the scope of the invention. Antibodies to LOS have been shown to protect in experimental rats against infection and to contribute to the bactericidal activity in children infected with *N. meningitidis* (Griffiss et al J Infect Dis 1984; 150: 71-79).

A problem associated with the use of LOS in a meningococcal vaccine, however, is its toxicity (due to its Lipid A moiety).

LOS is also present on the surface of meningococcal blebs. For many years efforts have been focused on developing meningococcal outer membrane vesicle (or bleb) based vaccines (de Moraes, J. C., Perkins, B., Camargo, M. C. et al. Lancet 340: 1074-1078, 1992; Bjune, G., Hoiby, E. A. Gronnesby, J. K. et al. 338: 1093-1096, 1991). Such vaccines have the advantage of including several integral outer-membrane proteins in a properly folded conformation which can elicit a protective immunological response when administered to a host. In addition, Neisserial strains (including *N. meningitidis* serogroup B—menB) excrete outer membrane blebs in sufficient quantities to allow their manufacture on an industrial scale. More often, however, blebs are prepared by methods comprising a 0.5% detergent (e.g. deoxycholate) extraction of the bacterial cells (e.g. EP 11243). Although this is desired due to the toxicity of LOS (also called endotoxin) as described above, it also has the effect removing most of the LOS antigen from the vaccine.

A further problem with using LOS as a vaccine antigen is that 12 LPS immunotypes exist with a diverse range of carbohydrate-structures (M. P. Jennings et al, Microbiology 1999, 145, 3013-3021; Mol Microbiol 2002, 43:931-43). Antibodies raised against one immunotype fail to recognise a different immunotype. Although effort has been focused on producing a generic "core" region of the oligosaccharide portions of the LOS immunotypes (e.g. WO 94/08021), the bactericidal activity of antibodies generated against the modified LOS is lost. Thus a vaccine may need to have many LOS components of different immunotype to be effective.

A further problem exists with the use of LOS (also known as LPS or lipopolysaccharide) as antigens in human vaccines, namely that they carry saccharide structures that are similar to human saccharide structures (for instance on human red blood cells), thus posing a safety issue with their use. Yet changing the LOS structure is problematic due to the structural sensitivity of the bactericidal effectiveness of the LOS antigen.

The present invention presents processes for ameliorating one or more of the above problems, and presents methods for making novel vaccines based on meningococcal LOS as a protective antigen, particularly when present on an outer membrane vesicle.

BRIEF DESCRIPTION OF THE DRAWINGS

FIG. 3 illustrates the following graphs: (A) anti-13 LOS ELISA, (B) serum bactericidal assays, and (C) LOS depletion.

FIG. 4 illustrates the following graphs: (A) Dilution of MAb 1B2-1B7 and (B) Dilution of MAb L3.7.9.

FIG. 5 illustrates the following graphs: (A) B1820 DOC 0.1%—antigenicity with MAb L379, (B) B1820 DOC 0.1%—antigenicity mice sera raised against B1820 DOC 0.5%, and (C) B1820 DOC 0.1%—antigenicity mice sera raised against B1820 DOC 0.1%.

FIG. 6 illustrates the following graphs: (A) anti-LNnT ELISA (IgG)-14Post III-AI(OH)3 and (B) anti-LNnT ELISA (IgG)-14Post III-AI(OH)$_3$+MPL.

DESCRIPTION OF THE INVENTION

The subject matter of and information disclosed within the publications and patents or patent applications mentioned in this specification are incorporated by reference herein.

Reference to "lipooligosaccharide" (or "LOS") may also be referred to as "lipopolysaccharide" or "LPS".

The terms "comprising", "comprise" and "comprises" herein is intended by the inventors to be optionally substitutable with the terms "consisting of", "consist of", and "consists of", respectively, in every instance.

The present inventors have found that shortening the LOS oligosaccharide structures leads to the loss of epitopes that can elicit a bacteriocidal immune response. Instead, the inventors have found that in order to use LOS most effectively in a vaccine formulation, the LOS oligosaccharide structure must be retained as much as possible, but a combination of just 2 LOS antigens can yield a universally effective Neisserial (preferably meningococcal) vaccine. A first aspect of the invention is an immunogenic composition for the prevention or treatment of Neisserial (preferably meningococcal or meningococcal B) disease comprising Neisserial (preferably meningococcal) LOS of immunotype L2 and LOS of immunotype L3. LOS may be isolated by either known purification procedures, or may be present in at least 2 outer membrane vesicle (or bleb) preparations derived from L2 and L3 Neisserial strains. In order to remove toxic loosely held LOS from the bleb preparation, but retain high levels of integrated LOS antigen in the bleb, it is preferred that the blebs are extracted using a low concentration of detergent—0-0.3%, preferably 0.05-0.2%, most preferably around 0.1%, preferably deoxycholate (or DOC). Such a combination of LOS antigens, particularly in a bleb vaccine, is surprisingly advantageous in being effective against over 90% of N. meningitidis strains.

The inventors have also found that the above bleb immunogenic compositions of the invention, and indeed any Neisserial (preferably gonococcal or meningococcal) derived bleb immunogenic composition, can have an enhanced effect of protective antigens (including LOS) on their surface if certain combinations of immunodominant outer membrane proteins are downregulated in expression (and preferably deleted). A second aspect of the invention is therefore a Neisserial bleb preparation derived from a neisserial strain which has had 2 or more of the following outer membrane proteins downregulated in expression, and preferably deleted, compared to the native, non-modified strain: PorA, PorB, OpA, OpC or PilC. Preferably PorA and OpA, PorA and OpC, OpA and OpC, or PorA & OpA & and OpC are downregulated or deleted. Downregulation (preferably deletion) of expression of FrpB has also been shown to be beneficial in enhancing the effect of cross-protective antigens—particularly in bleb preparations made from neisserial strains grown in iron limiting conditions. A Neisserial bleb derived from a strain with this mutation is thus a further embodiment of the invention, as are blebs derived from a combination of FrpB downregulation with one or more of the downregulations mentioned above. It is preferred that if PorA is downregulated PorB should not be downregulated, and vice versa.

The above mutations are beneficial in any Neisserial (preferably meningococcal, most preferably menB) strain from which bleb immunogenic compositions are to be derived, particularly those described herein, however it is preferred that L2 or L3 immunotype Neisserial (preferably meningococcal, most preferably menB) strains are used, typically extracted with a low DOC % extraction process as described herein. Preferably the bleb immunogenic compositions of the invention contain both L2 and L3 blebs where at least one (and preferably both) is deficient in the above combinations of immunodominant outer membrane proteins (or OMPs). Techniques for downregulating these genes are discussed in WO 01/09350 (incorporated by reference herein). Four different Opa genes are known to exist in the meningococcal genome (Aho et al. 1991 Mol. Microbiol. 5:1429-37), therefore where Opa is said to be downregulated in expression it is meant that preferably 1, 2, 3 or (preferably) all 4 genes present in meningococcus are so downregulated. Such downregulation may be performed genetically as described in WO 01/09350 or by seeking readily-found, natural, stable meningococcal strains that have no or low expression from the Opa loci. Such strains can be found using the technique described in Poolman et al (1985 J. Med. Micro. 19:203-209) where cells that are Opa$^-$ have a different phenotype to cells expressing Opa which can be seen looking at the appearance of the cells on plates or under a microscope. Once found, the strain can be shown to be stably Opa$^-$ by performing a Western blot on cell contents after a fermentation run to establish the lack of Opa.

Safety of the Above LOS Immunogenic Compositions

Figure 1:
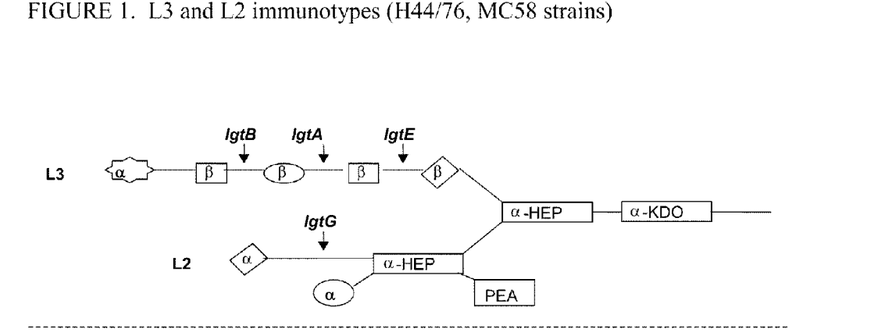
FIG. 1 illustrates a schematic of L3 and L2 immunotypes (H44/76, MC58 strains).

The safety of antibodies raised to L3 or L2 LOS has been questioned, due to the presence of a structure similar to the lacto-N-neotetraose oligosaccharide group (Galβ1-

Figure 2:
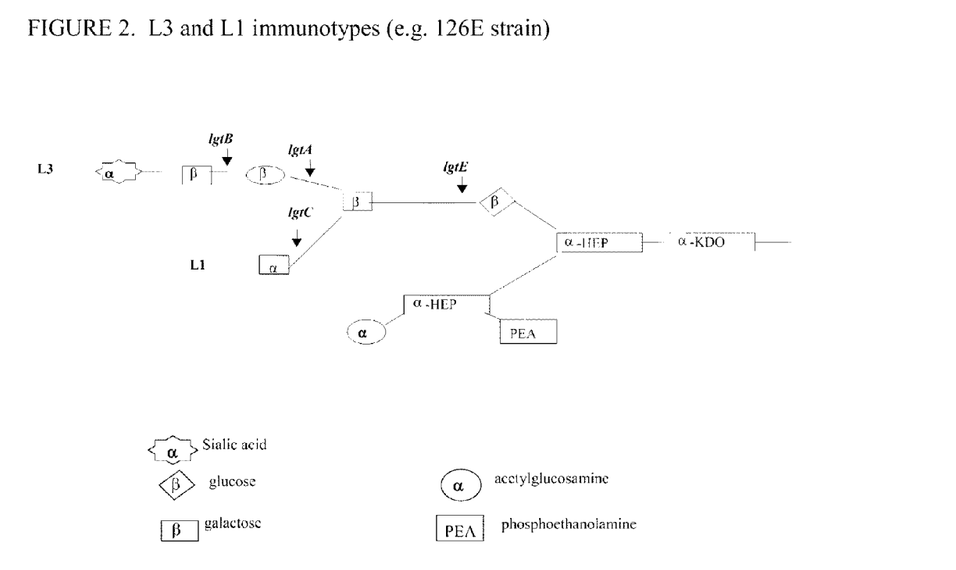
FIG. 2 illustrates a schematic of L3 and L1 immunotypes (126E strain).

4GlcNAcβ1-3Galβ1-4Glcβ1-; FIG. 1) present in human glycosphingolipids. Although a large number of people have been safely vaccinated with deoxycholate extracted vesicle vaccines containing residual amount of L3 LOS (G. Bjune et al, Lancet (1991), 338, 1093-1096; GVG. Sierra et al, NIPH ann (1991), 14, 195-210), if LOS is to be retained as an antigen as discussed herein, the deletion of a terminal part of the LOS saccharide structure has been found by the current inventors to be advantageous in preventing cross-reaction of the anti-LOS immune response with structures present at the surface of human tissues. In a preferred embodiment, inactivation of the lgtB gene results in an intermediate LOS structure in which the terminal galactose residue and the sialic acid are absent (see FIGS. 1 and 2, the mutation leaves a 4GlcNAcβ1-3Galβ1-4Glcβ1-structure in L2 and L3 LOS). Such intermediates could be obtained in an L3 and/or an L2 LOS strain. An alternative and less preferred (short) version of the LOS can be obtained by turning off the lgtE gene. A further alternative and less preferred version of the LOS can be obtained by turning off the lgtA gene. If such an lgtA⁻ mutation is selected it is preferred to also turn off lgtC expression to prevent the non-immunogenic L1 immunotype being formed.

LgtB$^-$ mutants are most preferred as the inventors have found that this is the optimal truncation for resolving the safety issue whilst still retaining an LOS protective oligosaccharide epitope that can still induce a bactericidal (and even cross-bactericidal) antibody response.

Therefore, the above L2 and/or L3 preparations (whether purified or in an isolated bleb) of the invention or meningococcal bleb preparations in general (particularly L2 and/or L3) are advantageously derived from a Neisserial strain (preferably meningococcal) that has been genetic engineered to permanently downregulate the expression of functional gene product from the lgtB, lgtA or lgtE gene, preferably by switching the gene off, most preferably by deleting all or part of the promoter and/or open-reading frame of the gene.

Preferably the neisserial strains of the invention are deficient in synthesising capsular polysaccharide.

Where the above bleb preparations of the invention are derived from a meningococcus B strain, it is particularly preferred that the capsular polysaccharide (which also contains human-like saccharide structures) is also removed. Although many genes could be switched off to achieve this, the inventors have advantageously shown that it is preferred that the bleb production strain has been genetically engineered to permanently downregulate the expression of functional gene product from the siaD gene (i.e. downregulating α-2-8 polysialyltransferase activity), preferably by switching the gene off, most preferably by deleting all or part of the promoter and/or open-reading frame of the gene. Such an inactivation is described in WO 01/09350. The siaD (also known as synD) mutation is the most advantageous of many mutations that can result in removing the human-similar epitope from the capsular polysaccharide, because it one of the only mutations that has no effect on the biosynthesis of the protective epitopes of LOS, thus being advantageous in a process which aims at ultimately using LOS as a protective antigen, and has a minimal effect on the growth of the bacterium. A preferred aspect of the invention is therefore a bleb immunogenic preparation as described above which is derived from an lgtE$^-$ siaD$^-$, an lgtA$^-$ siaD$^-$ or, preferably, an lgtB$^-$ siaD$^-$ meningococcus B mutant strain. The strain itself is a further aspect of the invention.

Although siaD$^-$ mutation is preferable for the above reasons, other mutations which switch off meningococcus B (or meningococcus in general) capsular polysaccharide synthesis may be used. Thus bleb production strain can be genetically engineered to permanently downregulate the expression of functional gene product from one or more of the following genes: ctrA, ctrB, ctrC, ctrD, synA (equivalent to synX and siaA), synB (equivalent to siaB) or synC (equivalent to siaC) genes, preferably by switching the gene off, most preferably by deleting all or part of the promoter and/or open-reading frame of the gene. The lgtE$^-$ mutation may be combined with one or more of these mutations. Preferably the lgtB$^-$ mutation is combined with one or more of these mutations. A further aspect of the invention is therefore a bleb immunogenic preparation as described above which is derived from such a combined mutant strain of meningococcus B (or meningococcus in general). The strain itself is a further aspect of the invention.

A Neisserial locus containing various lgt genes, including lgtB and lgtE, and its sequence is known in the art (see M. P. Jennings et al, Microbiology 1999, 145, 3013-3021 and references cited therein; J. Exp. Med. 180:2181-2190 [1994]; WO 96/10086).

Where full-length (non-truncated) LOS is to be used in the final product, it is desirable for LOS not to be sialylated (as such LOS generates an immune response against the most dangerous, invasive meningococcal B strains which are also unsialylated). In such case using a capsule negative strain which has a deleted synA (equivalent to synX and siaA), synB (equivalent to siaB) or synC (equivalent to siaC) gene is advantageous, as such a mutation also renders menB LOS incapable of being sialylated.

The above mutations are beneficial in any Neisserial (preferably meningococcal, most preferably menB) strain from which bleb immunogenic compositions are to be derived, particularly those described herein, however it is preferred that L2 or L3 immunotype Neisserial (preferably meningococcal, most preferably menB) strains are used, typically extracted with a low DOC % extraction process as described herein. Preferably the bleb immunogenic compositions of the invention contains both L2 and L3 blebs where at least one (and preferably both) is derived from strains deficient in the expression of the above genes.

The Toxicity of LOS

The above purified LOS or bleb immunogenic compositions of the invention may also be rendered less toxic by downregulating expression of certain genes in the bacterial production strain from which they are derived. Although such detoxification may not be necessary for intranasal immunization with native OMV (J. J. Drabick et al, Vaccine (2000), 18, 160-172), for parenteral vaccination detoxification would present an advantage. Preferably the LOS purified LOS or bleb immunogenic compositions of the invention are detoxified by genetically engineering the Neisserial production strain by mutation/modification/inactivation of the genes involved in LipidA biosynthesis, particularly those genes involved in adding secondary acyl chains to lipidA, in particular by downregulating the expression of functional gene product from the msbB and/or htrB genes, and preferably by switching the gene off, most preferably by deleting all or part of the promoter and/or open-reading frame of the gene. Alternatively (or in addition) the purified LOS or bleb immunogenic compositions can be derived from a Neisserial strain which has been genetically modified so that one or more of the following genes are upregulated (by introducing a stronger promoter or integrating an extra copy of the gene): pmrA, pmrB, pmrE and pmrF. Alternatively (or in addition) the purified LOS or bleb immunogenic compositions may be detoxified by adding non-toxic peptide functional equivalents of polymyxin B [a molecule with high affinity for Lipid A] to the compositions.

See WO 01/09350 for more detail on the above detoxification methods, and for relevant promoter/gene sequences and upregulation and downregulation methods. The msbB and htrB genes of *Neisseria* are also called lpxL1 and lpxL2, respectively, (see WO 00/26384) and deletion mutations of these genes are characterised phenotypically by the msbB⁻ mutant LOS losing one secondary acyl chain compared to wild-type (and retaining 4 primary and 1 secondary acyl chain), and the htrB⁻ mutant LOS losing both secondary acyl chains. Such mutations are preferably combined with mutations to ensure that the neisserial production strain is capsular polysaccharide deficient (see above) to ensure the optimal presentation of detoxified LOS on the bleb, or to aid the purification of the detoxified subunit LOS. See WO 93/14115, WO 95/03327, Velucchi et al (1997) J Endotoxin Res 4: 1-12, and EP 976402 for further details of non-toxic peptide functional equivalents of polymyxin B that may be used in the compositions of this invention—particularly the use of the peptide SAEP 2 (of sequence KTKCKFLKKC where the 2 cysteines form a disulphide bridge).

By "downregulating the expression of functional gene product" it is meant herein that additions, deletions or substitutions are made to the promoter or open reading frame of the gene in question such that the biosynthetic activity of the total gene product reduces (by 60, 70, 80, 90, 95 or most preferably 100%). Clearly frameshift mutations may be introduced, or weaker promoters substituted, however most preferably most or all of the open reading frame and/or promoter is deleted to ensure a permanent downregulation of the (active) gene product (as described in WO 01/09350).

The above mutations are beneficial in any Neisserial (preferably meningococcal, most preferably menB) strain from which bleb immunogenic compositions are to be derived, particularly those described herein, however it is preferred that L2 or L3 immunotype Neisserial (preferably meningococcal, most preferably menB) strains are used, typically extracted with a low DOC % extraction process as described herein. Preferably the bleb immunogenic compositions of the invention contains both L2 and L3 blebs where at least one (and preferably both) is derived from strains deficient in the expression of the above genes.

Further aspects of the invention include the above described genetically modified Neisserial (preferably meningococcal or gonococcal or meningococcal B) strains from which the LOS or bleb immunogenic preparations of the invention may be derived.

The LOS or LOS-Containing Bleb Preparations of the Invention

A further aspect of the invention is a LOS preparation (particularly any of those described above) isolated from the Neisserial strains of the invention. Preferably the isolated LOS (or LOS-containing bleb) is L2 or L3 immunotype, and preferably the immunogenic compositions of the invention comprise both L2 and L3 LOS (or bleb) preparations of the invention.

Such preparations may also be improved by conjugating the oligosaccharide portion of the above LOS (whether purified or present in a bleb preparation) to a carrier comprising a source of T-cell epitopes (thus rendering the LOS an even better [T-dependent] immunogen). A purified LOS preparation of the invention may alternatively (or in addition) be rendered a better antigen by presenting it in liposome formulations known in the art (see for instance WO 96/40063 and references cited therein).

The process of isolation of LOS from bacteria is well known in the art (see for instance the hot water-phenol procedure of Wesphal & Jann [Meth. Carbo. Chem. 1965, 5:83-91]). See also Galanos et al. 1969, Eur J Biochem 9:245-249, and Wu et al. 1987, Anal Bio Chem 160:281-289. Techniques for conjugating isolated LOS are also known (see for instance EP 941738 incorporated by reference herein).

For the purposes of this invention "a carrier comprising a source of T-cell epitopes" is usually a peptide or, preferably, a polypeptide or protein. Conjugation techniques are well known in the art. Typical carriers include protein D from non typeable *H. influenzae*, tetanus toxoid, diphtheria toxoid, CRM197, or outer membrane proteins present in bleb (particularly neisserial or meningococcal) preparations.

Preferred isolated LOS compositions of the invention are: a composition comprising L2 and L3 isolated LOS wherein the oligosaccharide portion of each LOS is optionally conjugated to a carrier comprising a source of T-cell epitopes, a composition comprising L2 or L3 LOS which has a structure consistent with it having been derived from a $lgtB^-$ meningococcal strain wherein the oligosaccharide portion of each LOS is optionally conjugated to a carrier comprising a source of T-cell epitopes, and most preferably a composition comprising L2 and L3 isolated LOS which have a structure consistent with them having been derived from an $lgtB^-$ meningococcal strain, wherein the oligosaccharide portion of each LOS is optionally conjugated to a carrier comprising a source of T-cell epitopes.

Preferably the LOS compositions of the invention have been detoxified. This may be done by known techniques of hydrazine or alkaline hydrolysis chemical treatments which remove acyl chains from the molecule (but which may reduce the protective efficacy of the molecule), but is preferably done by isolating the LOS from an $htrB^-$ or $msbB^-$ meningococcal mutant (as described above; particularly in capsule polysaccharide minus strains), or by adding a non-toxic peptide functional equivalent of polymyxin B [a molecule with high affinity to Lipid A] to the composition, in particular SAEP 2 (as described above).

The LOS of the invention may be administered in an isolated state (usually in the form of micelles if the lipid A moiety is still intact), or may be administered in a liposome. In such case outer membrane proteins may be added to the liposome, and the LOS may be conjugated intra-liposome to such outer membrane proteins to render the oligosaccharide a T-dependent antigen. This may be done with a similar chemistry as described for intra-bleb LOS cross-linking as described below.

Intra-Bleb Cross-Linking (Conjugation) of the Oligosaccharide Portion of LOS to Outer Membrane Proteins Present on the Surface of the Bleb Where LOS (in particular the LOS of the invention) is present in a bleb formulation the LOS is preferably conjugated in situ by methods allowing the conjugation of LOS to one or more outer membrane proteins also present on the bleb preparation (e.g. PorA or PorB in meningococcus). Thus a further aspect of the invention is a bleb preparation from a Gram-negative bacterial strain in the outer-membrane of which is integrated an outer-membrane protein conjugated to LOS. Although LOS may be added to a bleb preparation for conjugation, it is preferred that the LOS is naturally present on the surface of the bleb preparation.

This process can advantageously enhance the stability and/or immunogenicity (providing T-cell help) and/or antigenicity of the LOS antigen within the bleb formulation—thus giving T-cell help for the T-independent oligosaccharide immunogen in its most protective conformation—as LOS in its natural environment on the surface of the outer membrane. In addition, conjugation of the LOS within the bleb can result in a detoxification of the LOS (without wishing to be bound by theory, the Lipid A portion may be more stably buried in the outer membrane if conjugated thus being less available to cause toxicity). Thus the detoxification methods mentioned above of isolating blebs from htrB⁻ or msbB⁻ mutants, or by adding non toxic peptide functional equivalent of polymyxin B to the composition may not be required (but which may be added in combination for additional security).

The conjugated bleb preparations of the invention are typically such that the toxicity of the LOS in the bleb is reduced compared to the same blebs with the same amount of totally unconjugated LOS. LOS toxicity may be readily determined by a skilled person, for example using the LOS rabbit pyrogenicity assay in the European Pharmacopoeia (see Example 7).

The conjugated bleb preparations of the invention are advantageously such that the conjugated LOS has a conformation suitable for eliciting an immune response in a host, the sera from which is reactive (can bind) with unconjugated LOS—preferably present on the bacterium from which the bleb preparation was made, and most preferably in a bactericidal fashion in a SBA assay.

Where neisserial blebs are conjugated to LOS, and the blebs are derived from a strain downregulated in one or more immunodominant outer membrane proteins as described herein, it is preferred that if PorA is downregulated PorB should not be downregulated, and vice versa. This allows the majority of LOS to cross-link with a major outer membrane protein, and thus minimises any effect of conjugation on cross-protective minor outer membrane antigens present in the bleb.

In particular, the inventors have found that a composition comprising blebs wherein LOS present in the blebs has been conjugated in an intra-bleb fashion to outer membrane proteins also present in the bleb can form the basis of a vaccine for the treatment or prevention of diseases caused by the organism from which the blebs have been derived, wherein such vaccine is of reduced toxicity (preferably substantially non-toxic) and/or is capable of inducing a T-dependent bactericidal response against LOS in its native environment.

This invention therefore further provides such an intra-bleb LOS conjugated bleb preparation. By "intra bleb" it is meant that LOS naturally present in the bleb is conjugated to outer membrane protein present on the same bleb. Preferably the blebs have been derived from any Gram negative organism from which blebs can be produced (see WO 01/09350), preferably *Moraxella catarrhalis*, non-typeable *Haemophilus influenzae* or *Neisseria* (most preferably meningococcus).

Such bleb preparations may be isolated from the bacteria in question (see WO 01/09350), and then subjected to known conjugation chemistries to link groups (e.g. NH₂ or COOH) on the oligosaccharide portion of LOS to groups (e.g. NH₂ or COOH) on bleb outer membrane proteins. Cross-linking techniques using glutaraldehyde, formaldehyde, or glutaraldehyde/formaldehyde mixes may be used, but it is preferred that more selective chemistries are used such as EDAC or EDAC/NHS (J. V. Staros, R. W. Wright and D. M. Swingle. Enhancement by N-hydroxysuccinimide of water-soluble carbodiimide-mediated coupling reactions. Analytical Chemistry 156: 220-222 (1986); and Bioconjugates Techniques. Greg T. Hermanson (1996) pp 173-176). Other conjugation chemistries or treatments capable of creating covalent links between LOS and protein molecules that could be used in this invention are described in EP 941738.

Preferably the bleb preparations are conjugated in the absence of capsular polysaccharide. The blebs may be isolated from a strain which does not produce capsular polysaccharide (naturally or via mutation), or may be purified from most (more than 60, 70, 80, 90, or 99% removed) and preferably all contaminating capsular polysaccharide. In this way, the intra-bleb LOS conjugation reaction is much more efficient.

Preferably more than 5, 10, 20, 30, 40, 50, 60, 70, 80, 90, or 95% of the LOS present in the blebs is cross-linked/conjugated.

Preferably the blebs of the invention have been prepared such that the LOS content of the blebs is 3-30, 5-25, 10-25, 15-22, and most preferably around or exactly 20% LOS content as measured by silver staining after SDS-PAGE electrophoresis using purified LOS as a standard (see method of Tsai, J. Biol. Standardization (1986) 14:25-33). 20% LOS in meningococcal blebs can be achieved with a 0.1% low DOC extraction, which may remove loosely held LOS molecules, but conserve the majority of the antigen.

Where the intra-bleb conjugated blebs are derived from meningococcus, it is preferred that the strain from which they are derived is a mutant strain that cannot produce capsular polysaccharide (e.g. one of the mutant strains described above, in particular siaD⁻). It is also preferred that immunogenic compositions effective against meningococcal disease comprise both an L2 and L3 bleb, wherein the L2 and L3 LOS are both conjugated to bleb outer membrane proteins. Furthermore, it is preferred that the LOS structure within the intra-bleb conjugated bleb is consistent with it having been derived from an lgtB⁻ meningococcal strain. Most preferably immunogenic compositions comprise intrableb-conjugated blebs: derived from a L2 or L3 mutant meningococcal strain that cannot produce capsular polysaccharide and is lgtB⁻; comprising L2 and L3 blebs derived from mutant meningococcal strains that cannot produce capsular polysaccharide; comprising L2 and L3 blebs derived from mutant meningococcal strains that are lgtB⁻; or most preferably comprising L2 and L3 blebs derived from mutant meningococcal strains that cannot produce capsular polysaccharide and are lgtB⁻.

A typical L3 meningococcal strain that can be used for the present invention is the H44/76 menB strain. A typical L2 strain is the B16B6 menB strain or the 39E meningococcus type C strain or strain 760676.

As stated above, the blebs of the invention have been detoxified to a degree by the act of conjugation, and need not be detoxified any further, however further detoxification methods may be used for additional security, for instance by using blebs derived from a meningococcal strain that is htrB⁻ or msbB⁻ or adding a non-toxic peptide functional equivalent of polymyxin B [a molecule with high affinity to Lipid A] (preferably SEAP 2) to the bleb composition (as described above). Conjugation of LOS (particularly in an intra-bleb fashion) thus surprisingly exhibits a lower toxicity of LOS compared with preparations comprising the same amount of unconjugated LOS. Thus a general method for detoxifying blebs (particularly meningococcal) is further provided by means of intra-bleb conjugation of LOS to bleb outer membrane protein, and a method for detoxifying LOS is also provided by means of conjugating the LOS to bleb outer membrane protein.

In the above way meningococcal blebs and immunogenic compositions comprising blebs are provided which have as an important antigen LOS which is reduced in toxicity (and preferably substantially non-toxic), devoid of autoimmunity problems, has a T-dependent character, is present in its natural environment, and is capable of inducing a bactericidal antibody response against potentially more than 90% of meningococcal strains (in the case of L2+L3 compositions).

One or more of Men A, C, Y or W capsular polysaccharides or oligosaccharides (preferably at least MenC, or MenA and MenC, or Men C and MenY) may also be conjugated onto an outermembrane protein of the bleb of the invention as well. Although this could be done in the same reaction as LOS cross-linking, it is preferred that this is done in a separate (preferably later) reaction.

The process of optimal intra-bleb LOS conjugation is a further aspect of the present invention. Said process should incorporate the steps of isolating blebs from a Gram negative bacterium (preferably using a low % of DOC as described herein), carrying out chemistry suitable for conjugating LOS (preferably via its oligosaccharide moiety) present in the blebs to an outer membrane protein present on the same bleb, isolating the intra-bleb conjugated bleb preparation, and optionally formulating the intra-bleb conjugated bleb preparation with a further intra-bleb conjugated bleb preparation made by the same process but having a different LOS immunotype (preferably mixing L2 and L3 Neisserial/meningococcal blebs) and/or formulating the bleb preparation with a pharmaceutically acceptable excipient to make a vaccine composition.

Intrableb conjugation should preferably incorporate 1, 2 or all 3 of the following process steps: conjugation pH should be greater than pH 7.0, preferably greater than or equal to pH 7.5 (most preferably under pH 9); conditions of 1-5% preferably 2-4% most preferably around 3% sucrose should be maintained during the reaction; NaCl should be minimised in the conjugation reaction, preferably under 0.1M, 0.05M, 0.01M, 0.005M, 0.001M, and most preferably not present at all. All these process features make sure that the blebs remain stable and in solution throughout the conjugation process.

The EDAC/NHS conjugation process is a preferred process for intra-bleb conjugation. EDAC/NHS is preferred to formalydehyde which can cross-link to too high an extent thus adversely affecting filterability. EDAC reacts with carboxylic acids (such as KDO in LOS) to create an active-ester intermediate. In the presence of an amine nucleophile (such as lysines in outer membrane proteins such as PorB), an amide bond is formed with release of an isourea by-product. However, the efficiency of an EDAC-mediated reaction may be increased through the formation of a Sulfo-NHS ester intermediate. The Sulfo-NHS ester survives in aqueous solution longer than the active ester formed from the reaction of EDAC alone with a carboxylate. Thus, higher yields of amide bond formation may be realized using this two-stage process. EDAC/NHS conjugation is discussed in J. V. Staros, R. W. Wright and D. M. Swingle. Enhancement by N-hydroxysuccinimide of water-soluble carbodiimide-mediated coupling reactions. Analytical Chemistry 156: 220-222 (1986); and Bioconjugates Techniques. Greg T. Hermanson (1996) pp 173-176. Preferably 0.01-5 mg EDAC/mg bleb is used in the reaction, more preferably 0.05-1 mg EDAC/mg bleb. The amount of EDAC used depends on the amount of LOS present in the sample which in turn depends on the deoxycholate (DOC) % used to extract the blebs. At low % DOC (e.g. 0.1%), high amounts of EDAC are used (1 mg/mg and beyond), however at higher % DOC (e.g. 0.5%), lower amounts of EDAC are used (0.025-0.1 mg/mg) to avoid too much inter-bleb crosslinking.

A preferred process of the invention is therefore a process for producing intra-bleb conjugated LOS (preferably meningococcal) comprising the steps of conjugating blebs in the presence of EDAC/NHS at a pH between pH 7.0 and pH 9.0 (preferably around pH 7.5), in 1-5% (preferably around 3%) sucrose, and optionally in conditions substantially devoid of NaCl (as described above), and isolating the conjugated blebs from the reaction mix.

The reaction may be followed on Western separation gels of the reaction mixture using anti-LOS (e.g. anti-L2 or anti-L3) mAbs to show the increase of LOS molecular weight for a greater proportion of the LOS in the blebs as reaction time goes on.

Yields of 99% blebs can be recovered using such techniques.

EDAC was found to be an excellent intra-bleb cross-linking agent in that it cross-linked LOS to OMP sufficiently for improved LOS T-dependent immunogenicity, but did not cross link it to such a high degree that problems such as poor filterability, aggregation and inter-bleb cross-linking occurred. The morphology of the blebs generated is similar to that of unconjugated blebs (by electron microscope). In addition, the above protocol avoided an overly high cross-linking to take place (which can decrease the immunogenicity of protective OMPs naturally present on the surface of the bleb e.g. TbpA or Hsf).

Techniques for Isolating Blebs

Outer Membrane Vesicles (OMVs or blebs) of the invention can be isolated by many known techniques (Fredriksen et al, NIPH Annals (1991), 14, 67-79; Zollinger et al, J. Clin Invest (1979), 63, 836-848; Saunders et al, Infect Immun (1999), 67, 113-119; J. J. Drabick et al, Vaccine (1999), 18, 160-172). These divide into 2 main groups—techniques which use deoxycholate (about 0.5%) to extract blebs from meningococcus, and techniques that use low levels of deoxycholate (DOC) or no deoxycholate at all. DOC free process blebs have the interesting feature of maintaining high level of LOS in the OMV—which is advantageous in a vaccine where LOS is a protective antigen. Compared to DOC extracted blebs, the concentration of L3 Ags in OMV obtained by a DOC free process is approximately ten times higher. A detergent-free (preferably DOC-free) process of preparing blebs is preferred for the purposes of the processes of this invention for this reason, although extraction with a buffer containing low levels of detergent (preferably DOC) may also be advantageous in that the step would leave most of the tightly interacting LOS in the bleb whilst removing any more toxic loosely retained LOS. Typically 0-0.5% and preferably 0.02-0.4%, 0.04-3% or 0.06-2% detergent (preferably DOC) is used for bleb extraction, more preferably 0.08-0.15%, and most preferably around or exactly 0.1% is used to obtain an optimal amount of LOS to be stably present in the blebs. DOC free (or low DOC—0.3% DOC or under) extraction processes are particularly preferred where the LOS has been detoxified by one or more of the methods detailed above.

It is preferred that the LOS content of the blebs in all embodiments of the present invention is 3-30, 5-25, 10-25, 15-22, and most preferably around or exactly 20% LOS content as measured by silver staining after SDS-PAGE electrophoresis using purified LOS as a standard (see method of Tsai, J. Biol. Standardization (1986) 14:25-33). Using Nmen L3 LOS as a standard in this method, in general LOS content in Nmen L3 immunotype blebs extracted with 0.1% DOC is about 20% LOS, with 0.2% DOC is about 15% LOS, with 0.3% DOC is about 10% LOS, and with 0.5% DOC is about 5% LOS.

Vaccine Compositions

The immunogenic compositions of the invention may readily be formulated as vaccine compositions by adding a pharmaceutically acceptable excipient.

A process for making the Neisserial (preferably meningococcal) immunogenic compositions or vaccines of the invention is further provided comprising the steps of isolating, purified LOS of the invention (preferably L2 or L3) as described above or producing isolated blebs of the invention (preferably with an L2 or L3 immunotype) as described above, and formulating the LOS or blebs with a pharmaceutically acceptable excipient. Preferably purified LOS of both immunotype L2 and L3 of the invention, or blebs of both immunotype L2 and L3 of the invention, or a purified LOS of L2 and a bleb of L3 (or vice versa), are combined in a mixing step. Preferably the purified LOS or bleb of the invention has been conjugated as described above after isolation. An additional liposome formulation step may also be added for the purified LOS (using techniques known in the art—see for instance WO 96/40063 and references cited therein). Preferably bleb preparations are isolated by extraction with low (or no) concentrations of DOC (as described above).

Such L2 and L3 combination processes can yield a vaccine which is effective against almost all meningococcal B strains.

The above immunogenic compositions (or processes) may have added one or more (2, 3 or 4) meningococcal polysaccharides or oligosaccharides (either plain or conjugated to a carrier comprising T-cell epitopes, as described above) from serogroups A, C, Y or W to the composition. Preferably at least C is added (most preferably conjugated), and more preferably A and C or Y and C (preferably all conjugated) and most preferably A, C, Y and W (preferably all conjugated). Advantageously a conjugated *H. influenzae* B capsular polysaccharide or oligosaccharide is also included in the above compositions to generate a universal meningitis vaccine.

Preferably compositions consisting of or comprising compositions specifically individualised in WO 94/08021 are not claimed in the present invention.

Vaccine Formulations of the Invention

The immunogenic compositions of the invention may be formulated with a suitable adjuvant to generate vaccine compositions of the invention.

Suitable adjuvants include an aluminium salt such as aluminum hydroxide gel (alum) or aluminium phosphate (preferably aluminium hydroxide), but may also be a salt of calcium (particularly calcium carbonate), iron or zinc, or may be an insoluble suspension of acylated tyrosine, or acylated sugars, cationically or anionically derivatised polysaccharides, or polyphosphazenes.

Suitable Th1 adjuvant systems that may be added include, Monophosphoryl lipid A, particularly 3-de-O-acylated monophosphoryl lipid A (or other non-toxic derivatives of LPS), and a combination of monophosphoryl lipid A, preferably 3-de-O-acylated monophosphoryl lipid A (3D-MPL) [or non toxic LPS derivatives] together with an aluminium salt (preferably aluminium phosphate). An enhanced system involves the combination of a monophosphoryl lipid A and a saponin derivative particularly the combination of QS21 [or other saponin] and 3D-MPL [or non toxic LPS derivative] as disclosed in WO 94/00153, or a less reactogenic composition where the QS21 [or saponin] is quenched with cholesterol as disclosed in WO96/33739. A particularly potent adjuvant formulation involving QS21, 3D-MPL and tocopherol in an oil in water emulsion is described in WO95/17210 and is a preferred formulation that may be added. Other adjuvants that may be added comprise a saponin, more preferably QS21 and/or an oil in water emulsion and tocopherol. Unmethylated CpG containing oligo nucleotides (WO 96/02555) may also be added Vaccine preparation is generally described in Vaccine Design ("The subunit and adjuvant approach" (eds Powell M. F. & Newman M. J.) (1995) Plenum Press New York).

An immunoprotective dose of vaccines can be administered via the systemic or mucosal route. These administrations may include injection via the intramuscular, intraperitoneal, intradermal or subcutaneous routes; or via mucosal administration to the oral/alimentary (preferably intra-nasal administration), respiratory, genitourinary tracts. Typically bleb quantity in each vaccine dose is selected as an amount which induces an immunoprotective response without significant, adverse side effects in typical vaccinees. Such amount will vary depending upon which specific immunogen is employed and how it is presented. Generally, it is expected that each dose will comprise 1-100 µg of each bleb, preferably 5-50 µg, and most typically in the range 5-25 µg.

Further Improvements to the Bleb Immunogenic Compositions of the Invention

The above bleb compositions of the invention may be further improved in efficacy in vaccines of the invention if the Neisserial strain from which they are derived (including gonococcus, and preferably meningococcus, most preferably *N. meningitidis* B) have one or more of the following genes (encoding protective antigens) upregulated by inserting further copies of the gene into the genome, or introducing a stronger promoter upstream of the existing gene, or any of the other ways discussed in WO 01/09350 which are capable of inducing modified strains to make over 1.2, 1.5, 2, 3, 5 or 10 times the level of antigen as compared to the unmodified strain: NspA (WO 96/29412), Hsf or truncates thereof (WO 99/31132 & WO 01/55182; also known as NhhA), Hap (PCT/EP99/02766), OMP85 (WO 00/23595), PilQ (PCT/EP99/03603), PldA (PCT/EP99/06718), FrpB (WO 96/31618), TbpA (WO92/03467, U.S. Pat. No. 5,912,336, WO93/06861 and EP586266), TbpB (WO93/06861 and EP586266), NadA (Comanducci et al J. Exp. Med. 2002 195; 1445-1454; NMB 1994), FrpA/FrpC or portions in common between these antigens involving 5 or more repeat sequences (WO 92/01460; Thompson et al., (1993) J. Bacteriol. 175:811-818; Thompson et al., (1993) Infect. Immun 61:2906-2911), LbpA, LbpB (PCT/EP98/05117), FhaB (WO98/02547 SEQ ID NO 38 [nucleotides 3083-9025]), HasR (PCT/EP99/05989), lipo02 (PCT/EP99/08315), Tbp2 (WO 99/57280; NMB 0460), MltA (WO 99/57280; NMB 0033), TspA (WO 00/03003), TspB (WO 00/03003), ctrA (PCT/EP00/00135), MafA (NMB 0652), MafB (NMB0643), Omp26 (NMB 0181), Adhesin X (NMB 0315), Adhesin Y (NMB 0995), Adhesin Z (NMB 1119), and OstA (NMB 0280). Examples of NMB sequences can be found in the database at www.neisseria.org. Where Hsf is mentioned herein, the term may be substitutable in every instance for Hsf truncates—in particular those disclosed in WO 01/55182.

It is particularly preferred if both Hsf and TbpA (Low or High, or both Low and High molecular weight forms [EP 586266]), or Hsf and OMP85, or OMP85 and TbpA (Low or High, or both Low and High molecular weight forms), or NspA and Hsf, or NspA and OMP85, or NspA and TbpA (Low or High, or both Low and High molecular weight forms) are both upregulated. Where 2 blebs are comprised in the composition, it is preferred that each bleb has different upregulations. If TbpA High and Low are both to be upregulated, it is preferable that these are upregulated in 2 separate blebs present in the composition derived from 2 strains that naturally comprise the 2 forms of TbpA. Most preferably, the 2 strains have L2 and L3 LOS immunotypes. TbpA may be upregulated genetically or by growing the neisserial/meningococcal production strains in iron limited conditions for instance in the presence of 50-70 µM Desferal (deferoxamine mesylate, available from Sigma). If the latter approach is taken, it is preferred that the FrpB gene expression is downregulated (preferably deleted) as this variable antigen may become immunodominant in blebs isolated from meningococcal strains isolated in Iron limited conditions.

In a preferred embodiment, the composition of the invention comprises an L3 bleb from a lgtB⁻ capsular polysaccharide⁻msbB⁻ strain preferably upregulated in TbpA High and Hsf and an L2 bleb from a lgtB⁻ capsular polysaccharide⁻ msbB⁻ strain preferably upregulated in TbpA Low and Omp85. More preferably both blebs are additionally downregulated in PorA and/or FrpB expression, and optionally OpC and/or OpA expression. The blebs are most preferably isolated via a low DOC process as described above, and the LOS in both blebs is intra-bleb cross-linked to outer membrane protein.

Ghost or Killed Whole Cell Vaccines

The inventors envisage that the above compositions and vaccines concerning blebs can be easily extended to processes concerning ghost or killed whole cell preparations and vaccines (with identical advantages). Methods of making ghost preparations (empty cells with intact envelopes) from Gram-negative strains are well known in the art (see for example WO 92/01791). Methods of killing whole cells to make inactivated cell preparations for use in vaccines are also well known. Therefore the compositions and vaccines involving blebs described throughout this document are envisioned to be applicable to the same compositions or vaccines comprising equivalent ghost and killed whole cell preparations of the invention.

Serum Bactericidal Assays on the Compositions of the Invention

The serum bactericidal assay is the preferred method to assess synergistic relationships between antigens when combined in an immunogenic composition of the invention.

Such a synergistic response may be characterised by the SBA elicited by the combination of antigens being at least 50%, two times, three times, preferably four times, five times, six times, seven times, eight times, nine times and most preferably ten times higher than the SBA elicited by each antigen separately. Preferably SBA is measured against a homologous strain from which the antigens are derived and preferably also against a panel of heterologous strains. (See below for a representative panel for instance BZ10 (B:2b:P1.2) belonging to the A-4 cluster; B16B6 (B:2a:P1.2) belonging to the ET-37 complex; and H44/76 (B:15:P1.7,16)). SBA is the most commonly agreed immunological marker to estimate the efficacy of a meningococcal vaccine (Perkins et al. J Infect Dis. 1998, 177:683-691). Satisfactory SBA can be ascertained by any known method. SBA can be carried out using sera obtained from animal models, or from human subjects.

A preferred method of conducting SBA with human sera is the following. A blood sample is taken prior to the first vaccination, two months after the second vaccination and one month after the third vaccination (three vaccinations in one year being a typical human primary vaccination schedule administered at, for instance, 0, 2 and 4 months, or 0, 1 and 6 months). Such human primary vaccination schedules can be carried out on infants under 1 year old (for instance at the same time as Hib vaccinations are carried out) or 2-4 year olds or adolescents may also be vaccinated to test SBA with such a primary vaccination schedule. A further blood sample may be taken 6 to 12 months after primary vaccination and one month after a booster dose, if applicable.

SBA will be satisfactory for an antigen or bleb preparation with homologous bactericidal activity if one month after the third vaccine dose (of the primary vaccination schedule) (in 2-4 year olds or adolescents, but preferably in infants in the first year of life) the percentage of subjects with a four-fold increase in terms of SBA (antibody dilution) titre (compared with pre-vaccination titre) against the strain of meningococcus from which the antigens of the invention were derived is greater than 30%, preferably greater than 40%, more preferably greater than 50%, and most preferably greater than 60% of the subjects.

Of course an antigen or bleb preparation with heterologous bactericidal activity can also constitute bleb preparation with homologous bactericidal activity if it can also elicit satisfactory SBA against the meningococcal strain from which it is derived.

SBA will be satisfactory for an antigen or bleb preparation with heterologous bactericidal activity if one month after the third vaccine dose (of the primary vaccination schedule) (in 2-4 year olds or adolescents, but preferably in infants in the first year of life) the percentage of subjects with a four-fold increase in terms of SBA (antibody dilution) titre (compared with pre-vaccination titre) against three heterologous strains of meningococcus is greater than 20%, preferably greater than 30%, more preferably greater than 35%, and most preferably greater than 40% of the subjects. Such a test is a good indication of whether the antigen or bleb preparation with heterologous bactericidal activity can induce cross-bactericidal antibodies against various meningococcal strains. The three heterologous strains should preferably have different electrophoretic type (ET)-complex or multilocus sequence typing (MLST) pattern (see Maiden et al. PNAS USA 1998, 95:3140-5) to each other and preferably to the strain from which the antigen or bleb preparation with heterologous bactericidal activity is made or derived. A skilled person will readily be able to determine three strains with different ET-complex which reflect the genetic diversity observed amongst meningococci, particularly amongst meningococcus type B strains that are recognised as being the cause of significant disease burden and/or that represent recognised MenB hypervirulent lineages (see Maiden et al. supra). For instance three strains that could be used are the following: BZ10 (B:2b:P1.2) belonging to the A-4 cluster; B16B6 (B:2a:P1.2) belonging to the ET-37 complex; and H44/76 (B:15:P1.7,16) belonging to the ET-5 complex, or any other strains belonging to the same ET/Cluster. Such strains may be used for testing an antigen or bleb preparation with heterologous bactericidal activity made or derived from, for instance, meningococcal strain CU385 (B:4:P1.15) which belongs to the ET-5 complex. Another sample strain that could be used is from the Lineage 3 epidemic clone (e.g. NZ124 [B:4:P1.7,4]). Another ET-37 strain is NGP165 (B:2a:P1.2).

Processes for measuring SBA activity are known in the art. For instance a method that might be used is described in WO 99/09176 in Example 10C. In general terms, a culture of the strain to be tested is grown (preferably in conditions of iron depletion—by addition of an iron chelator such as EDDA to the growth medium) in the log phase of growth. This can be suspended in a medium with BSA (such as Hanks medium with 0.3% BSA) in order to obtain a working cell suspension adjusted to approximately 20000 CFU/ml. A series of reaction mixes can be made mixing a series of two-fold dilutions of sera to be tested (preferably heat-inactivated at 56° C. for 30 min) [for example in a 50 μl/well volume] and the 20000 CFU/ml meningococcal strain suspension to be tested [for example in a 25 μl/well volume]. The reaction vials should be incubated (e.g. 37° C. for 15 minutes) and shaken (e.g. at 210 rpm). The final reaction mixture [for example in a 100 μl volume] additionally contains a complement source [such as 25% final volume of pretested baby rabbit serum, or human serum for human serology], and is incubated as above [e.g. 37° C. for 60 min]. A sterile polystyrene U-bottom 96-well microtiter plate can be used for this assay. A aliquot [e.g. 10 µl] can be taken from each well using a multichannel pipette, and dropped onto Mueller-Hinton agar plates (preferably containing 1% Isovitalex and 1% heat-inactivated Horse Serum) and incubated (for example for 18 hours at 37° C. in 5% $CO_2$). Preferably, individual colonies can be counted up to 80 CFU per aliquot. The following three test samples can be used as controls: buffer+bacteria+complement; buffer+bacteria+inactivated complement; serum+bacteria+inactivated complement. SBA titers can be straightforwardly calculated using a program which processes the data to give a measurement of the dilution which corresponds to 50% of cell killing by a regression calculation.

All references or patent applications cited within this patent specification are incorporated by reference herein.

EXAMPLES

The examples below are carried out using standard techniques, which are well known and routine to those of skill in the art, except where otherwise described in detail. The examples are illustrative, but do not limit the invention.

Example 1

Examples describing deletions genes encoding proteins involved in B capsular polysaccharide production of meningococcus B, the deletion of the PorA gene, the upregulation of various protective outer membrane proteins on the surface of meningococcal blebs, the downregulation of immunodominant proteins or biosynthetic enzymes, and processes for isolating blebs are described in WO 01/09350.

Example 2

LOS: a Key Cross-Protective Antigen

To assess the role of LOS as a potential cross-protective antigen, H44/76 wild type (WT) meningococcus B strain (expressing L3 LOS) and a modified H44/76 strain expressing a "galE$^-$-like LOS" (with a short structure as for a lgtE$^-$ LOS) were used to produce blebs according two different processes. The first process used 0.1% DOC in order to have high levels of LOS in blebs, the second used 0.5% DOC to have low levels of LOS in the resulting blebs.

Mice received three injections (on Day 0, 21 and 28) by IM route of 5 µg of blebs adsorbed on $Al^{3+}$ salts (aluminium phosphate) and 3D-MPL per dose. Blood samples were taken 14 days after the third injection.

Figure 3A:
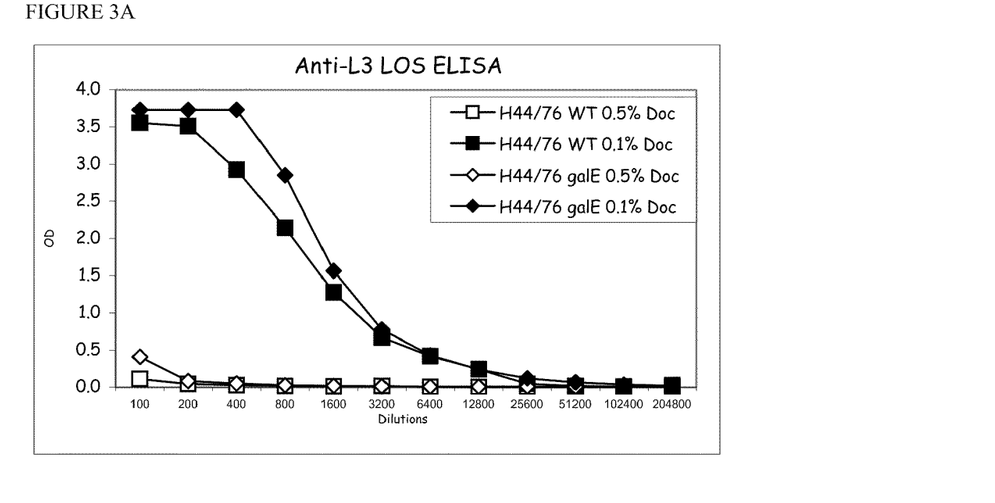

Anti-L3 LOS ELISA was done on pooled sera and using purified L3 LOS. The results in FIG. 3A clearly show that 0.1% DOC process produced blebs able to elicit an anti-LOS response in mice. This demonstrates that galE$^-$ LOS and L3 LOS are able to induce the production of antibodies. 0.5% DOC on the other hand extracted too much LOS in order for it to act as a key antigen in the bleb vaccine.

Serum Bactericidal Assays

SBA were performed on individual sera using different NmenB strains: the homologous WT H44/76 strain, a PorA (−) H44/76 strain, and two heterologous strains (based on sero-subtype) Cu385 and NZ124. These four strains express an L3 LOS. A fifth strain was added. Compared to H44/76, this strain (B16B6) is heterologous not only for PorA but also for LOS (it is an immunotype L2 strain).

Figure 3B:
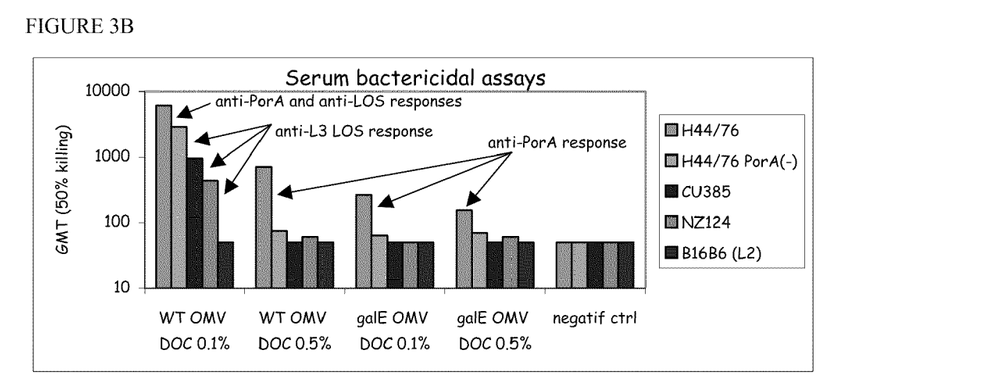

The results in FIG. 3B indicate a cross-bactericidal response against only L3 strains but only with the DOC 0.1% WT blebs. No cross-bactericidal response is observed for DOC 0.1% galE$^-$ blebs and DOC 0.5% WT blebs. In addition, it is well known that the bactericidal response induced by PorA antibodies is sero-type dependent. This is also observed in this experiment with either DOC 0.5% WT blebs or galE$^-$ blebs and also with SBA data done with the PorA(−) H44/76 strain.

All these results suggest that the cross-bactericidal response induced by blebs containing high percentage of L3 LOS is due to the production of Abs directed against the LOS antigen.

Only the L3 LOS (and not the galE$^-$ LOS) is able to elicit the production of bactericidal antibodies. Although, in ELISA a good anti-LOS response is observed with DOC 0.1% galE$^-$ blebs, this response is not biologically relevant (no SBA).

In addition, it seems also that the response is LOS immunotype specific as anti-L3 LOS Abs kill only L3 strains but not L2 strains, indicating that an optimal vaccine should ideally contain L3 and L2 LOS for optimal coverage.

Depletion Experiment

In order to demonstrate that the response induced by WT DOC 0.1% blebs is mainly due to anti-LOS antibodies, pools of sera were depleted with different concentrations of purified L3 LOS. After depletion, sera were used in a bactericidal assay against the homologous WT H44/76 strain.

Figure 3C:
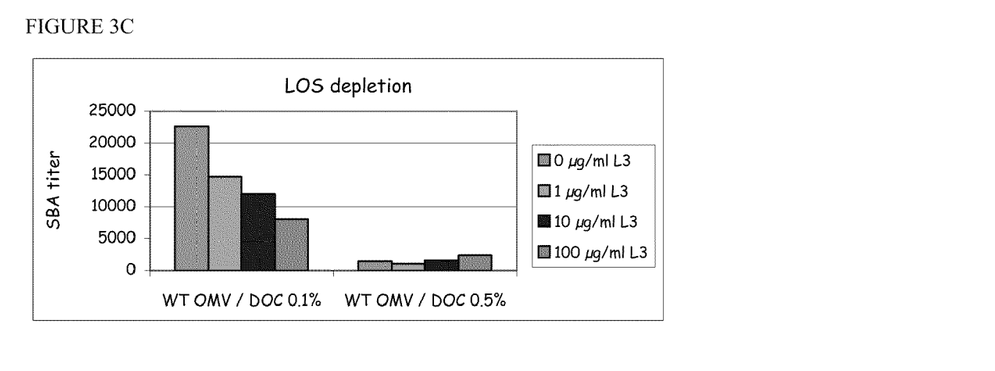

The results obtained (see FIG. 3C) with sera raised against DOC 0.1% WT blebs show a clear dose-range inhibition, demonstrating that most of the antibodies induced by this preparation are directed against LOS (confirming SBA results generated with PorA(−) H44/76 strain). In contrast, the response induced by WT DOC 0.5% is not directed against LOS as demonstrated by SBA done with PorA(−) H44/76 strain and also indicated by LOS depletion.

This result is likely to follow for L2 LOS.

Example 3

Experiments with L3 and Intermediate (lgtB$^-$) DOC Free Blebs (Non-Detoxified LOS) Induced Cross-Bactericidal Antibodies The MC58 meningococcal derivative strain used is B:P1.7.16, opc-, siaD-. This strain was genetically modified to express either L3 (strain 2G2) or an intermediate epitope (strain 2G EcoN1b-1, as 2G2 but additionally lgtB$^-$) or an LPS in short version (strain C6, which is lgtE$^-$). OMV were produced according either a normal high (0.5%) DOC process or DOC free process.

Mice (10 per group) were immunized three times by the intra-muscular route on Day 0, 20 and 28. They received 1 or 10 µg (protein content) of blebs formulated on $Al(OH)_3$. Blood samples were taken on day 28 (post II) and day 42 (post III).

Bactericidal assays were done on pooled sera and using homologous strains (MC58 and H44/76) and two heterologous strains (M97250687 and M9725078) with baby rabbit serum as source of exogenous complement.

The following table summarizes the results (bactericidal titers for 50% killing):

|  |  | Strain and serotype | | | |
| --- | --- | --- | --- | --- | --- |
| Antigen | Blood samples | MC58 P1.7.16 | H44/76TT P1.7.16 | M97250687 P1.19.15 | M97252078 P1.4 |
| c6 no doc 10 ug IM | Post II | >2560 | >2560 | >2560 | 98 |
| c6 no doc 10 ug IM | Post III | 1,353 | >2560 | >2560 | 90 |
| c6 no doc 1 ug IM | Post II | 247 | 620 | 247 | <20 |
| c6 no doc 1 ug IM | Post III | 411 | 878 | 748 | <20 |
| 2g2 no doc 10 ug IM | Post II | >320 | >2560 | >2560 | >2560 |
| 2g2 no doc 10 ug IM | Post III | >2560 | >2560 | >2560 | 1407 |
| 2g2 no doc 1 ug IM | Post II | >2560 | >2560 | >2560 | 119 |
| 2g2 no doc 1 ug IM | Post III | >2560 | >2560 | >2560 | 348 |
| 2gecoN1b-1 no doc 10 ug IM | Post II | >2560 | >2560 | >2560 | 1162 |
| 2gecoN1b-1 no doc 10 ug IM | Post III | >2560 | >2560 | >2560 | 1213 |
| 2gecoN1b-1 no doc 1 ug IM | Post II | 1,151 | >2560 | 1,696 | 22 |
| 2gecoN1b-1 no doc 1 ug IM | Post III | 2,220 | >2560 | 1,947 | 135 |
| c6 doc 10 ug IM | Post II | 308 | 248 | 341 | <20 |
| c6 doc 10 ug IM | Post III | 189 | 104 | 400 | <20 |
| c6 doc 1 ug IM | Post II | 33 | 43 | 63 | <20 |
| c6 doc 1 ug IM | Post III | NC (>20) | 24 | 156 | <20 |
| 2g2 doc 10 ug IM | Post II | NC (>20) | 25 | 360 | <20 |
| 2g2 doc 10 ug IM | Post III | 201 | <20 | 647 | <20 |
| 2g2 doc 1 ug IM | Post II | 275 | <20 | 299/644 | <20 |
| 2g2 doc 1 ug IM | Post III | 237 | <20 | 728 | <20 |
| 2gecoN1b-1 doc 10 ug IM | Post II | 573 | 31 | 685 | <20 |
| 2gecoN1b-1 doc 10 ug IM | Post III | NC (>40) | 21 | 1,140 | <20 |
| 2gecoN1b-1 doc 1 ug IM | Post II | 261 | NC | 118 | <20 |
| 2gecoN1b-1 doc 1 ug IM | Post III | 348 | NC | 692 | <20 |

Clearly, the presence of L3 (2g2) or intermediate (2geconlb-1) epitope induces cross-bactericidal antibodies, while blebs from truncated LPS strain (C6) induce lower level of cross-reacting antibodies. This was particularly illustrated when 1 μg of OMV was injected.

Moreover, as shown with OMV purified with DOC, reducing the LPS content of blebs reduces the induction of cross-bactericidal antibodies. Aside from increased LPS, it is possible that DOC free blebs may also advantageously retain some proteins loosely interacting with the OMVs such as lipoproteins.

Example 4

Intra-Bleb Cross-Linking of L3 LOS and Outer-Membrane Protein

The MenB blebs used were derived from an H44/76 strain (LOS immunotype L3) that was SiaD⁻ (thus not expressing capsular polysaccharide) and PorA⁻. Two different strains were used: a full L3 (strain B1717, siad(−) PorA (−) Full L3) and a truncated L3 (strain B1727, siad(−) PorA (−) lgtB(−) TrL3).

The EDAC/NHS conjugation process was used according to known methods to cross-link LOS and OMP within the blebs to render the oligosaccharide component of LOS a T-dependent antigen (EDAC/NHS was preferred to formaly-dehyde which was found to cross-link to too high an extent thus adversely affecting filterability). EDAC reacts with carboxylic acids to create an active-ester intermediate. In the presence of an amine nucleophile, an amide bond is formed with release of an isourea by-product. However, the efficiency of an EDAC-mediated reaction may be increased through the formation of a Sulfo-NHS ester intermediate. The Sulfo-NHS ester survives in aqueous solution longer than the active ester formed from the reaction of EDAC alone with a carboxylate. Thus, higher yields of amide bond formation may be realized using this two-stage process. EDAC/NHS conjugation is discussed in J. V. Staros, R. W. Wright and D. M. Swingle. Enhancement by N-hydroxysuccinimide of water-soluble carbodiimide-mediated coupling reactions. Analytical Chemistry 156: 220-222 (1986); and Bioconjugates Techniques. Greg T. Hermanson (1996) pp 173-176.

The reaction mixture contained 1.5 mg Sulfo-NHS and 5 mg EDAC in 3% sucrose (for bleb stability) in a volume of 1 mL. Blebs were present in a ratio of 0.025 mg EDAC/mg blebs. Blebs were present in a concentration of 2 mg/ml and pH was adjusted to 7.5 with HCl 0.1 N or NaOH 0.1N.

The reaction was left for 4 hours at room temperature, and the mixture was dialysed against 2 mM phosphate buffer containing 3% sucrose, pH 7.5. The mixture was then filtered on Sterivex G10 0.22 μm. A yield of 99% blebs was recovered.

The reaction could be followed on a Western blot using anti-L3 mAb. Through the reaction the low MW LOS becomes fainter and a new higher MW band appears on the gel. This higher MW band seems to predominate and may represent the majority of the conjugated LOS becoming covalently linked to PorB.

EDAC was found to be an excellent intra-bleb cross-linking agent in that it cross-linked LOS to OMP irreversibly, and sufficiently for improved LOS T-dependent immunogenicity, but did not cross link it to such a high degree that problems such as poor filterability, aggregation and inter-bleb cross-linking occurred. The morphology of the blebs generated is similar to that of unconjugated blebs (as observed by electron micrograph). In addition, the above protocol avoided an overly high cross-linking to take place (which can decrease the immunogenicity of protective OMPs naturally present on the surface of the bleb e.g. TbpA).

Example 5

L3 and Truncated (Intermediate, lgtB−) L3 can Induce Production of Bactericidal Abs which Recognise Truncated (Intermediate lgtB−; TrL3) L3 LOS OMV (blebs) were produced from MenB strain H44/76 siaD-PorA-L3 or from H44/76 siad-porA-TrL3. Two different extractions were performed; the percentage of DOC used was either 0.1 or 0.5%. Two different adjuvant formulations were also evaluated: Al(OH)3 or Aluminium phosphate+3D-MPL. Mice (OF1 female mice, 6-8 weeks old, 30 per group) were injected 3 times (at day 0, 21 and 28) by IM route (5 µg blebs/injection). SBA were collected on post II (day 28) and post III (day 42) sera (pooled sera or individual sera).

The geometric mean titre and pooled sera titre for 50% cell killing was greater for sera induced by blebs extracted with 0.1% DOC as compared with 0.5% DOC extraction. This is likely to be explained by the fact that there tends to be 2.5 times as much LOS in the former blebs as compared with the latter. There was no significant difference between SBA of sera induced with blebs containing full L3 LOS or truncated L3 LOS. There is an increase in SBA if blebs are adjuvanted with aluminium phosphate+3D-MPL as compared with aluminium hydroxide.

Sera depletion experiments were also done. Sera were depleted using 1 mg/mL purified L3 or trL3 LOS and then SBA were performed on these depleted sera. The results showed that bactericidal Abs (containing anti-L3 antibodies) can be almost entirely depleted by trL3 LOS pre-treatment of sera, and bactericidal Abs (containing anti-trL3 antibodies) can be almost entirely depleted by L3 LOS pre-treatment of sera. Anti-L3 bactericidal Abs are thus able to react with trL3 LOS, and anti-trL3 bactericidal Abs are thus able to react with L3 LOS. Furthermore, the specificity of bactericidal Abs for a LOS structure present in both L3 and trL3 LOS has thus been demonstrated.

In conclusion, we have demonstrated that TrL3 structure (in OMVs) is able to induce production of bactericidal Abs against L3 strains. In combination with the depletion experiments, we have shown that TrL3 and L3 LOS are very close structures on an immunological basis, and trL3 can be used to generate Ab capable of killing L3 strains.

Example 6

TrL3 Solves the Potential Problem of Autoimmunity with the Full L3 Structure

If L3 and trL3 structures are so closely related immunologically in terms of protective antibodies, is there any difference between the structures with respect to the possible autoimmunity issues associated with L3 (and L2) LOS [through the lacto-N-neotetraose moiety]? We have addressed this issue by looking at whether cold agglutinins are able to recognise trL3 LOS?

MAb 1B2-1B7 (J Bio Chem 256 (1981) 10967-10972; and ATCC deposit number TIB-189) is known to agglutinate human adult red blood cells (RBC) at low temperatures and react with LNnT (lacto-N-neotetraose). It is a typical cold agglutinin.

This monoclonal antibody was used in the following experiment in conjunction with a MabL3.7.9 monoclonal antibody which is capable of killing L3 meningococcal strains.

These two mAbs were used in ELISA with microplates precoated with poly-L-lysine (1 µg/ml, 2 h at 37° C.) and then coated with purified L3 or purified TrL3 LOS (5 µg, overnight at 4° C.). The plates were then saturated with BSA (1%, 30 min at room temperature). Thereafter a standard ELISA was carried out with each of the 2 antibodies.

Figure 4A:
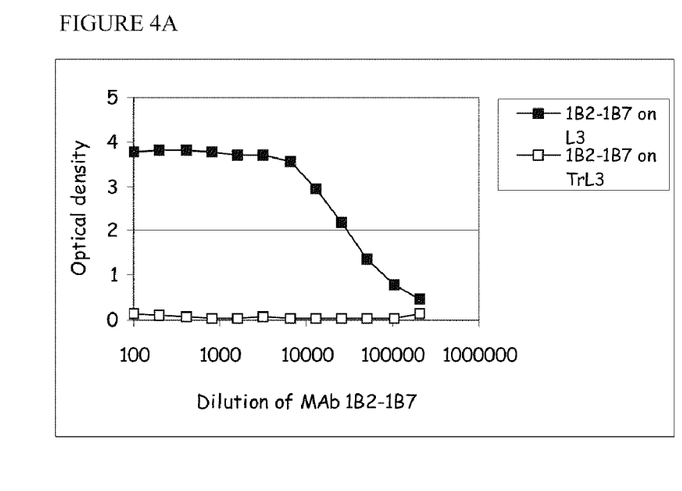
Figure 4B:
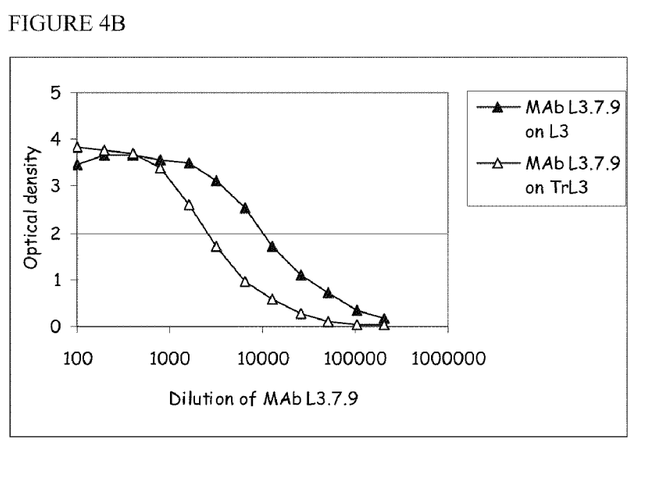

The results (FIG. 4) clearly show that Mab L379 reacts with L3 and TrL3 (FIG. 4B) but 1B2-1B7 reacts only against L3 LOS (FIG. 4A). Thus, we can say that TrL3 is not recognised by cold agglutinin which reacts against structures containing LNnT tetrasaccharide (such as L3 LOS and human red blood cells).

TrL3 LOS thus has the optimal characteristics of being long enough to retain protective epitopes, but short enough to lose epitopes that might have human autoimmune implications.

There is no reason to suggest that this should not also be the case for the truncated L2 (lgtB−) LOS structure proposed in this patent application.

Example 7

Impact of Cross-Linking on the Pyrogenicity/Antigenicity of B1820 DOC 0.1% Blebs Blebs (from strain B1820; which is derived from H44/76 with siaD(−) PorA(−) FrpB(−) truncated Hsf upregulated, Truncated L3 through lgtB(−) mutation strain, cultured in the presence of desferral, the blebs being extracted with DOC 0.1%) were cross-linked using different concentrations of EDAC (the more EDAC present, the more the blebs are cross-linked). The cross-linking is intra-bleb as shown by sterile filtration of the blebs.

LOS content in the blebs is 18% as measured by silver staining after SDS-PAGE electrophoresis using purified Nmen L3 LOS as a standard (Tsai, J. Biol. Standardization (1986) 14:25-33). In general LOS content in blebs extracted with 0.1% DOC is about 20% LOS, with 0.2% DOC is about 15% LOS, with 0.3% DOC is about 10% LOS, and with 0.5% DOC is about 5% LOS. In general blebs comprising 10% unconjugated LOS or more are unacceptably pyrogenic.

Pyrogenicity in Rabbits

Two formulations were tested (blebs adsorbed on $Al(OH)_3$ or $AlPO_4$) and rabbits received 500 ng/kg by the IV route in a pyrogenicity test as described in the European Pharmacopea.

The results clearly show (in the table below) a positive impact of the intra-bleb cross-link on the pyrogenicity of blebs. The same batch of blebs was used as a control or cross-linked with different EDAC concentrations. The more the blebs were cross-linked (more EDAC) the less they were pyrogenic. This was observed for two different formulations.

|  | Formulation | | |
| --- | --- | --- | --- |
| Treatment | $Al(OH)_3$ | $AlPO_4$ | Both formulation$ |
| not cross-linked | 3.1* | 2.8 | 5.9 |
| EDAC 0.05£ | 2.7 | 2.2 | 4.9 |
| EDAC 0.2 | 1.7 | 1.7 | 3.4 |
| EDAC 1 | 1.5 | 1.4 | 2.9 |

£EDAC concentration: mg of EDAC per mg of blebs
*sum of individual temperature (° C.) increase (3 rabbits per group)
$sum of six rabbits (3 from $Al(OH)_3$ group and 3 for $AlPO_4$ group)

Antigenicity of Cross-Linked Blebs

The antigenicity of the above blebs (non-adsorbed) were assessed to determine whether the cross-link has any impact on the antigenicity of the blebs. The different preparations of blebs (cross-linked or not) were coated on a microplate (10 µg/ml, overnight at 4° C.). After washing and saturation, serial dilution of MAb L379 or sera from mice immunized with B1820 DOC 0.1 or 0.5% were added to the plate (30 min at room temperature with shaking). The fixation of antibodies on coated blebs were revealed using anti-mouse Ig coupled to biotin then using a streptavidine-peroxydase complex followed by a revelation using OPD and $H_2O_2$. The density of each microwell was measured using a microplate reader.

Figure 5A:
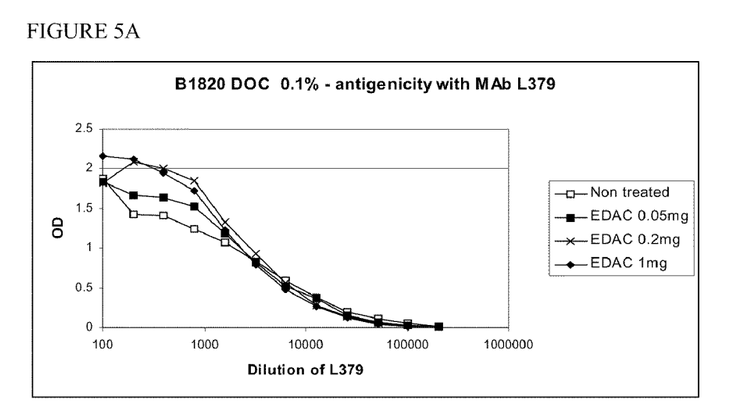

The results show that MAb L379 (directed against L3 LOS but also able to react with TrL3 LOS (the lgtB− mutant) and bactericidal against L3 strains) recognizes equivalently non-treated (unconjugated) B1820 blebs and the different cross-linked blebs (whatever the concentration of EDAC used). See FIG. 5A. The higher response obtained with EDAC 0.2 and 1 could reflect a better anchoring of LOS in the blebs or at least a better stability of LOS in cross-linked blebs at these EDAC concentrations.

Figure 5B:
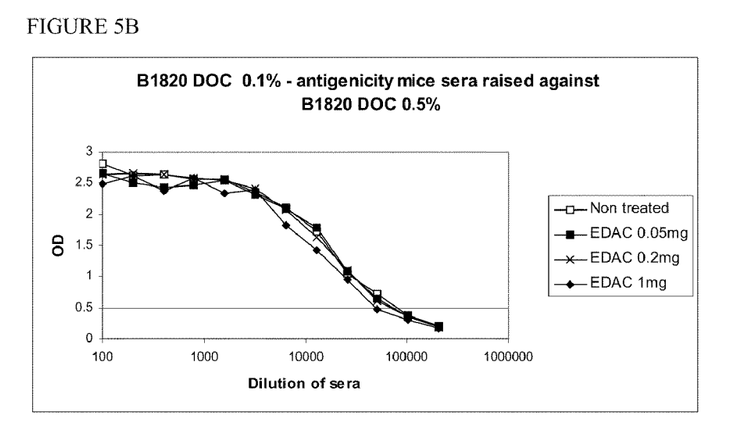
Figure 5C:
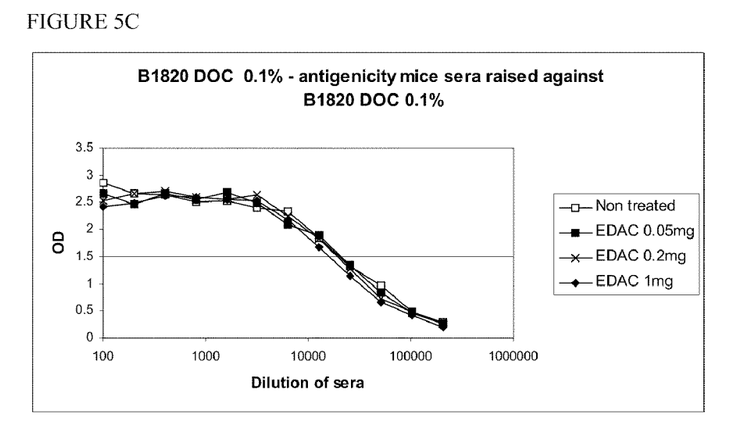

Mice sera were also used to assess the antigenicity of these blebs. Two different sera were used; the first was obtained from mice immunized with B1820 DOC 0.5% blebs (blebs with low LOS content ≦8% inducing mainly anti-protein antibodies). The second serum was obtained from mice immunized with B1820 DOC 0.1% blebs (blebs with LOS content ≧15%, inducing cross-bactericidal Abs mainly directed against LOS). As observed with L379 MAb, the results obtained with these two sera (FIGS. 5B and 5C, respectively) did not show any difference between non-treated (unconjugated) blebs and cross-linked blebs (whatever the concentration of EDAC used).

In conclusion, it seems that the antigenicity of LOS was not affected by the cross-linking and that the "global" antigenicity of blebs was also not modified by EDAC treatment. Immunogenicity experiments in mice are ongoing to confirm that cross-linking (with high concentrations of EDAC) does not destroy the immunogenicity of key protective antigens. Nevertheless, preliminary results (Example 8) show where cross-linking was done with EDAC 0.025 on DOC 0.5% extracted blebs indicate an increase in the immunogenicity of these blebs after EDAC treatment.

Example 8

Immunogenicity of Cross-Linked Blebs (EDAC 0.025 mg Chemistry)

In this experiment blebs were produced from the B1727 strain. This strain is a genetically modified H44/76 strain, which is siaD(−) PorA(−) trL3 (lgtB−) Hsf+TbpA upregulated. The blebs were extracted using 0.5% DOC. Mice were immunised three times (on Day 0, 21 and 28) by the IM route. Per injection, they received 5 μg of blebs adsorbed on Al(OH)$_3$.

Serum bactericidal assay was done against H44/76 strain on individual sera taken 14 days after the third injection. The results show a positive impact of EDAC treatment on the number of responders (No of mice with SBA titre>100): 37% of responders for EDAC treated blebs and only 17% with non-modified blebs.

The absence of 3D-MPL in formulation, and the relatively low percentage of LOS in the bleb preparations (around 5%) after 0.5% DOC extraction explain the low responses.

| Mice | B1727 SiaD (−) PorA (−) TrL3 TbpA-Hsf Cross-link "EDAC" | Blebs B1727 SiaD (−) PorA (−) TrL3 TbpA-Hsf No treatment |
|---|---|---|
| GMT | 52 | 27 |
| SBA on pools | 249 | 60 |
| Responders | 11/30 | 5/30 |

An anti-Hsf ELISA was also performed to determine if the cross-link has an impact on the immunogenicity of this protein. The results (obtained on pooled sera) indicate that the cross-link has no impact on IgG anti-Hsf response. No IgM were detected.

| | anti-Hsf ELISA | |
|---|---|---|
| | IgM | IgG |
| B1727 Siad(−) PorA(−) TbpA-Hsf TrL3 Cross-link EDAC | 50 | 18140 |
| B1727 Siad(−) PorA(−) TbpA-Hsf TrL3 | 50 | 15627 |
| Negative control | 50 | 50 |

Example 9

TrL3 LOS Data

The following experiment assessed:
the impact of TrL3 (lgtB(−)L3 LOS) on the induction of Abs able to react with LNnT (lacto-N-neotetraose);
the induction of bactericidal antibodies of the above construct.

Blebs were produced from two genetically modified H44/76 strains. Both were siaD( ) PorA(−) but one produced aWT L3 LOS and the second one a TrL3 LOS (lgtB(−)). These blebs were produced according to two different processes in order to have high LOS content (around 18%, using DOC 0.1% extraction) or low LOS content (close to 5%, using DOC 0.5% extraction).

Mice were immunized three times (on Day 0, 21 and 28) by the IM route with 5 μg of blebs (per injection) adsorbed on Al(OH)$_3$ with or without 3D-MPL.

Anti-LNnT ELISA

Method: Microplates were coated with LNnT conjugated to human serum albumin via a spacer (ADH) (5 μg of conjugate per ml in PBS, 100 μl per microwell). After an over-night incubation at 4° C., plates were washed and saturated with PBS-BSA 1% (40 min at room temp.). After washing, serially diluted in PBS-0.2% BSA-0.05% Tween20 were added (30 min at RT). Fixation of IgG to LNnT was revealed by anti-mouse-IgG coupled to peroxydase (Jackson) followed by incubation with OPDA and $H_2O_2$.

Results: The positive control is 1B2-1B7 MAb. This MAb reacts with LNnT, and with L3 LOS (but not TrL3 LOS) (see previous example) and it agglutinates human red blood cells. The negative control (−) is sera form mice immunized with adjuvant alone.

Figure 6A:
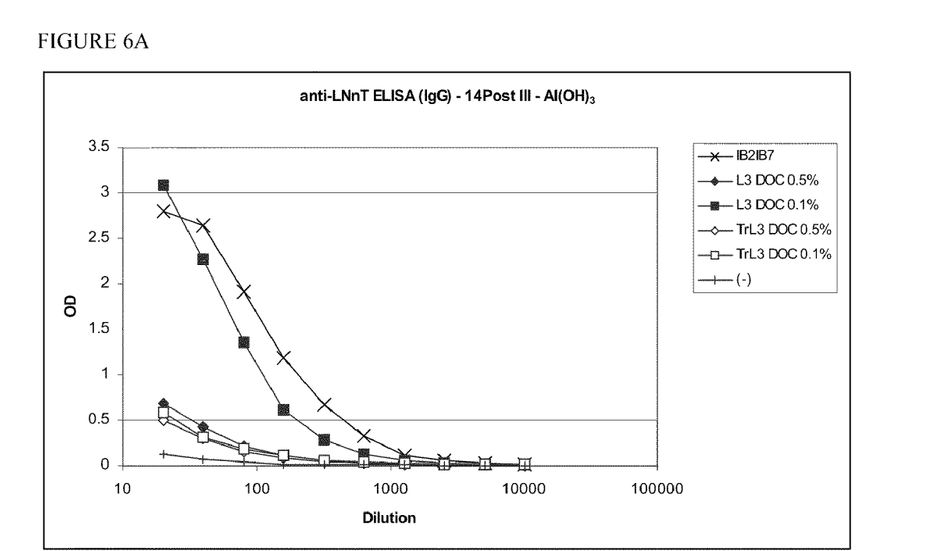
Figure 6B:
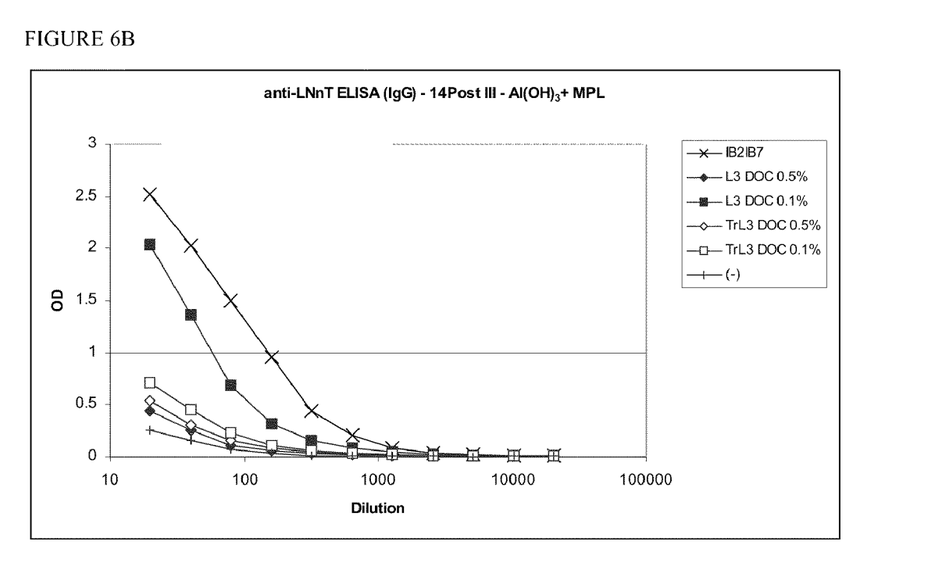

The results (FIG. 6) clearly show that only L3 blebs with a high LOS content (DOC 0.1%) induce the production of IgG able to react with LNnT. Tr L3 blebs, with a similar LOS content, do not induce the production of IgG directed against LNnT, as do not both blebs preparations containing low amount of LOS (DOC 0.5%).

SBA on H44/76 Strain

SBA assays against the H44/76 strain were performed on individual sera taken 14 days after the third injection. The results clearly show below that trL3 (lgtB(−)) LOS blebs induce similar levels of bactericidal antibodies than L3 LOS (see GMT but also the number of mice with SBA titer>1/100 (=SC))

| Formulation | | L3 Blebs | | TrL3 Blebs | |
|---|---|---|---|---|---|
| | | DOC 0.5% | DOC 0.1% | DOC 0.5% | DOC 0.1% |
| Al(OH)$_3$ + MPL | GMT | 331 | 4125 | 1029 | 3204 |
| | SC | 19/30 | 29/30 | 27/30 | 30/30 |
| Al(OH)$_3$ | GMT | 169 | 2029 | 138 | 828 |
| | SC | 14/30 | 29/30 | 13/30 | 30/30 |

Example 10

FrpB Knock-Out

The following data are a summary of two preclinical experiments.

In these experiments, two genetically modified H44/76 strains were used to produce blebs using 0.1% DOC. Blebs obtained by this process have an LOS content close to 20%.

The two H44/76 strains were the following:

B1733: siaD(−) PorA(−) Tr (Truncated) Hsf upregulated lgtB(−)

B1820: siaD(−) PorA(−) Tr (Truncated) Hsf upregulated lgtB(−) FrpB(−)

Blebs were produced after strains were grown in the presence of desferral to upregulate the production of iron dependent proteins such as LbpA/B, TbpA/B, FrpB (in B1733), etc.

These different bleb preparations were adsorbed on Al(OH)$_3$ and injected into mice by the IM route twice, three weeks apart. Blood samples were taken 7 days after the second administration. Mice received per injection 5 µg of blebs.

SBA Results

Bactericidal assays were done on three L3 strains (the homologous wild type strain H44/76 and two heterologous L3 strains: NZ124 and M97250687). The results clearly show that FrpB(−) (knock-out) (B1820) blebs induce a better heterologous cross-bactericidal response (high titers and better seroconversion SC) than FrpB(+) blebs (B1733). The homologous response, although lowered by the FrpB deletion, is still satisfactory.

These data suggest that FrpB is a major driver in the immune response elicited by blebs, but, as this outer membrane protein is highly variable, antibodies directed against this protein are only able to induce the killing of the homologous stain. Deletion of FrpB in the bleb production strain is therefore an advantageous means of improving the coverage of the bleb vaccine produced.

| Blebs | H44/76 GMT | H44/76 SC | M97250687 GMT | M97250687 SC | NZ124 GMT | NZ124 SC |
|---|---|---|---|---|---|---|
| B1733 | 1518 | 30/30 | 151 | 11/30 | 70 | 4/29 |
| B1820 | 781 | 19/30 | 1316 | 24/30 | 276 | 19/30 |

Example 11

Impact of the msbB (lpxL1) Mutation on the Pyrogenicity of Blebs

Two NmenB strains were used for this evaluation:
control strain which is galE(−) [and thus unable to make capsular polysaccharide]
msbB mutant strain: which is galE(−) and msbB(−)

Blebs were produced from these two strains using 0.1% of DOC in order to have more than 15% LOS content in the OMVs (blebs). As stated in previous examples, bleb preparations with higher than 10% LOS content are not satisfactory from a pyrogenicity point of view and fail the rabbit pyrogenicity assay of the European Pharmacopoeia.

The above blebs were formulated on Al(OH)$_3$ (50 µg of OMVs/500 µg of Al3+ salts) for a pyrogenicity assay in rabbits (500 ng of blebs/kg injected by IV route).

The results below clearly demonstrate that the deletion of msbB (particularly in a strain unable to make capsular polysaccharide) allows production of blebs that are non-pyrogenic in rabbits even for LOS content higher than 15%.

| Blebs | Dilution | Individual t° increase (° C.) | Sum of t° | Conclusion |
|---|---|---|---|---|
| Control DOC 0.1% | 0.5 µg/kg | 0.7-1.4-1.2 | 3.3 | FAIL |
| msbB(−) DOC 0.1% | 0.5 µg/kg | 0.1-0.2-0.2 | 0.5 | PASS |

European Pharmacopoeia rules:
"PASS" if sum of individual t° < 1.15° C.
"Fail if not repeat" if sum of individual t° between 1.15° C. and 2.65° C.
"Fail" if sum of individual t° > 2.65° C.

CONCLUSION

A composition comprising L3 and L2 blebs derived from meningococcal strains which have the lgtB(−) and msbB(−) mutations and are extracted with lower (e.g. 0.1%) deoxycholate concentrations provides a strong basis for an effective, safe vaccine against meningococcus B. The bleb production strains are ideally capsular polysaccharide synthesis deficient, and the blebs have LOS which is intra-bleb cross-linked to outer membrane protein. Either or both of PorA(−) and FrpB(−) are additionally helpful in improving cross-bactericidal effectiveness, as are Hsf and/or TbpA antigen upregulations.

The invention claimed is:

1. An isolated Neisserial bleb preparation from a engineered Neisserial strain in which the expression of functional FrpB gene product is reduced at least 80% in comparison with that of the native strain from which said engineered Neisserial strain is derived, wherein the reduction of expression of the functional FrpB gene product in the engineered Neisserial strain results from at least one addition, deletion, or substitution within the FrpB promoter, the FrpB open reading frame, or both the FrpB promoter and the FrpB open reading frame.

2. The isolated Neisserial bleb preparation of claim 1, wherein the reduction of expression of the functional FrpB gene product results from at least one deletion within the FrpB promoter, the FrpB open reading frame, or both the FrpB promoter and the FrpB open reading frame.

3. The isolated Neisserial bleb preparation of claim 1, wherein the engineered Neisserial is additionally engineered to reduce the expression of at least one outer membrane protein gene in comparison with the native strain from which said engineered Neisserial strain is derived, wherein said at least one outer membrane protein gene is selected from PorA, PorB, OpA, OpC, and PilC.

4. The isolated Neisserial bleb preparation of claim 3, wherein said reduction of expression of at least one outer membrane protein gene products results from one or more deletions within the outer membrane protein gene promoter, the outer membrane protein gene open reading frame, or both the outer membrane protein gene promoter and the outer membrane protein gene open reading frame.

5. The isolated Neisserial bleb preparation of claim 3, wherein the engineered Neisserial strain is additionally engineered to reduce the expression of functional gene product from at least two outer membrane protein genes, wherein said at least two outer membrane protein genes are:
  (a) PorA and OpA;
  (b) PorA and OpC; or
  (c) OpA and OpC.

6. The isolated Neisserial bleb preparation of claim 3, wherein the engineered Neisserial strain is additionally engineered to reduce the expression of functional gene product from at least three outer membrane protein genes, wherein said at least three outer membrane protein genes are PorA, OpA, and OpC.

7. The isolated Neisserial bleb preparation of claim 1, wherein said preparation has been derived from an engineered Neisserial strain with an L2 LOS immunotype or an engineered Neisserial strain with an L3 LOS immunotype, and wherein the engineered Neisserial strain is lgtB⁻.

8. The isolated Neisserial bleb preparation of claim 1, wherein the Neisserial strain is meningococcal.

9. The isolated Neisserial bleb preparation of claim 8 wherein the Neisserial strain is serogroup B.

10. The isolated Neisserial bleb preparation of claim 1, wherein the engineered Neisserial strain is additionally engineered to reduce the expression of at least one capsular polysaccharide gene in comparison with the native strain from which said engineered Neisserial strain is derived, wherein said at least one capsular polysaccharide gene is selected from ctrA, ctrB, ctrC, ctrD, synA, synB, synC, and siaD.

11. The isolated Neisserial bleb preparation of claim 10 wherein at least one capsular polysaccharide gene is siaD.

12. The isolated Neisserial bleb preparation of claim 1, wherein the engineered Neisserial strain is additionally engineered to reduce the expression of functional gene product from at least one lipid A gene in comparison with the native strain from which said engineered Neisserial strain is derived, wherein said at least one lipid A gene is selected from msbB and htrB.

13. The isolated Neisserial bleb preparation of claim 12, wherein at least one lipid A gene is htrB.

14. The isolated Neisserial bleb preparation of claim 1, wherein the engineered Neisserial strain is additionally engineered to increase the expression of functional gene product from at least one outer membrane protein antigen gene selected from NspA, TbpA low, TbpA high, Hsf, Hap, OMP85, PilQ, NadA, LbpA, and MltA at least 2 times in comparison with the level of the outer membrane protein antigen in the native strain from which said engineered Neisserial strain is derived, wherein the increase in expression of the at least one outer membrane protein in the engineered Neisserial strain results from inserting further copies of the outer membrane protein antigen gene, introducing a stronger promoter upstream of the existing outer membrane protein antigen gene, or both inserting further copies of the outer membrane protein antigen gene and introducing a stronger promoter upstream of the existing outer membrane protein antigen gene.

15. An immunogenic composition comprising the isolated Neisserial bleb preparation of claim 1 and a pharmaceutically acceptable excipient.

16. The immunogenic composition of claim 15 wherein said composition additionally comprises an adjuvant.

17. The immunogenic composition of claim 16 wherein said adjuvant is selected from aluminum hydroxide, 3D-MPL, and aluminum phosphate.

18. The immunogenic composition of claim 15, wherein said composition additionally comprises one or more conjugated capsular polysaccharides or oligosaccharides derived from a strain selected from meningococcus serogroup A, meningococcus serogroup C, meningococcus serogroup W-135, meningococcus serogroup Y, and *H. influenzae* type b.

19. An engineered Neisserial strain in which the expression of functional FrpB gene product is reduced 80% in comparison with that of the native strain from which said engineered Neisserial strain is derived, wherein the reduction of expression of functional FrpB gene product in the engineered Neisserial strain results from at least one addition, deletion, or substitution within the FrpB promoter, the FrpB open reading frame, or both the FrpB promoter and the FrpB open reading frame.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Neisseria meningitidis

<400> SEQUENCE: 1

Lys Thr Lys Cys Lys Phe Leu Lys Lys Cys
1               5                   10